US006794141B2

(12) United States Patent
Erlander et al.

(10) Patent No.: US 6,794,141 B2
(45) Date of Patent: Sep. 21, 2004

(54) NUCLEIC ACID AMPLIFICATION

(75) Inventors: Mark G. Erlander, Encinitas, CA (US); Ranelle C. Salunga, San Diego, CA (US)

(73) Assignee: Arcturus Bioscience, Inc., Mountain View, CA (US)

( * ) Notice: Subject to any disclaimer, the term of this patent is extended or adjusted under 35 U.S.C. 154(b) by 0 days.

(21) Appl. No.: 10/062,857

(22) Filed: Oct. 25, 2001

(65) Prior Publication Data

US 2003/0022194 A1 Jan. 30, 2003

Related U.S. Application Data

(60) Provisional application No. 60/298,847, filed on Jun. 15, 2001, and provisional application No. 60/257,801, filed on Dec. 22, 2000.

(51) Int. Cl.$^7$ ............................. C12Q 1/68; C12P 19/34

(52) U.S. Cl. ........................ 435/6; 435/91.2; 435/91.52

(58) Field of Search ...................... 435/6, 91.2, 91.52, 435/91.21, 91.51; 514/44; 536/23.1, 24.1, 25.3, 27

(56) References Cited

U.S. PATENT DOCUMENTS

| | | | |
|---|---|---|---|
| 4,415,732 A | 11/1983 | Caruthers et al. | ............. 536/27 |
| 4,458,066 A | 7/1984 | Caruthers et al. | ............. 536/27 |
| 4,582,789 A | 4/1986 | Mullis et al. | ................... 435/6 |
| 4,683,194 A | 7/1987 | Saiki et al. | ..................... 435/6 |
| 4,683,195 A | 7/1987 | Mullis et al. | .................. 435/6 |
| 4,725,677 A | 2/1988 | Koster et al. | ................. 536/27 |
| 4,786,600 A | 11/1988 | Kramer et al. | ............. 435/235 |
| 4,973,679 A | 11/1990 | Caruthers et al. | ............. 536/27 |
| 4,980,460 A | 12/1990 | Molko et al. | ................. 536/23 |
| 5,130,238 A | 7/1992 | Malek et al. | ................. 435/91 |
| 5,169,766 A | 12/1992 | Schuster et al. | ............. 435/91 |
| 5,399,491 A | 3/1995 | Kacian et al. | ........... 435/91.21 |
| 5,409,818 A | 4/1995 | Davey et al. | ............ 435/91.21 |
| 5,437,990 A | 8/1995 | Burg et al. | ................. 435/91.2 |
| 5,480,784 A | 1/1996 | Kacian et al. | ........... 435/91.21 |
| 5,545,522 A * | 8/1996 | Van Gelder et al. | ............. 435/6 |
| 5,554,516 A | 9/1996 | Kacian et al. | ........... 435/91.21 |
| 5,648,211 A | 7/1997 | Fraiser et al. | .................... 435/6 |
| 5,654,142 A | 8/1997 | Kievits et al. | .................... 435/6 |
| 5,716,785 A | 2/1998 | Van Gelder et al. | ............. 435/6 |
| 5,744,312 A | 4/1998 | Mamone et al. | ................ 435/6 |
| 5,766,849 A | 6/1998 | McDonough et al. | .......... 435/6 |
| 5,891,636 A | 4/1999 | Van Gelder et al. | ............. 435/6 |
| 5,914,229 A | 6/1999 | Loewy | ........................... 435/6 |
| 5,932,451 A | 8/1999 | Wang et al. | .............. 435/91.21 |
| 6,027,923 A | 2/2000 | Wallace | ..................... 435/91.2 |
| 6,110,711 A | 8/2000 | Serafini et al. | ........... 435/91.21 |
| 6,132,997 A * | 10/2000 | Shannon | .................. 435/91.21 |
| 6,297,365 B1 * | 10/2001 | Adams et al. | ............. 536/23.1 |
| 2002/0137709 A1 * | 9/2002 | Lin et al. | ..................... 514/44 |
| 2003/0022318 A1 * | 1/2003 | Lin et al. | ................... 435/91.2 |

FOREIGN PATENT DOCUMENTS

| | | |
|---|---|---|
| EP | 50424 | 8/1985 |
| EP | 201184 | 3/1986 |
| EP | 237362 | 3/1987 |
| EP | 258017 | 8/1987 |
| EP | 84796 | 5/1990 |
| EP | 0320308 B1 | 11/1993 |
| WO | WO 89/01050 | 2/1989 |

OTHER PUBLICATIONS

Agarwal et al. "Site Specific Functionalization of Oligo-nucleotides for Attaching Two Different Reporter Groups-"Nucleic Acids Research 18(18):5419–5423 (1990).
Altschul et al. "Basic Local Alignment Search Tool" J. Mol. Biol. 215:403–410 (1990).
Beaucage et al. "Advances in the Synthesis of Oligonucle-otides by the Phosphoramidite Approach" Tetrahedron 48(12):2223–2311 (1992).
Chamberlin et al. "Bacteriophage DNA–Dependent RNA Polymerases" Chapter 4 *In The Enzymes* vol. 15; Boyer, ed. Academic Press, N.Y. pp. 87–108 (1982).
Eberwine. "Amplification of mRNA Populations Using aRNA Generated from Immobilized Oligo(dT)–T7 Primed cDNA" BioTechniques 20:584–591 (1996).
Guatelli et al. "Isothermal, In Vitro Amplification of Nucleic Acids by a Multienzyme Reaction Modeled After Retroviral Replication " Proc. Natl. acad. Sci. U.S.A. 87:1874–1878 (1990).
Hampson et al. "Directional Random Oligonucleotide Primed (DROP) Global Amplification of cDNA: Its Appli-cation to Subtractive cDNA Cloning" Nucl. Acids Res. 24(23):4832–4835 (1996).
Hughes et al. "Expression Profiling Using Microarrays Fabricated by an Ink–Jet Oligonucleotide Synthesizer" Nature Biotechnology 19:342–347 (2001).
Lockhart et al. "Expression Monitoring by Hybridization to High–Density Oligonucleotide Arrays" Nature Biotechnol-ogy 14:1675–1680 (1996).
Mullis et al. "Specific Enzymatic Amplification of DNA In Vitro: The Polymerase Chain Reaction" Cold Spring Harbor Symposia on Quantitative Biology 51:263–273 (1986).
Ozaki et al. "The Estimation of Distances Between Specific Backbone–Labeled Sites in DNA Using Flourescence Reso-nance Energy Transfer" Nucleic Acids Research 20(19):5205–5214 (1992).

(List continued on next page.)

*Primary Examiner*—Kenneth R. Horlick
*Assistant Examiner*—Joyce Tung
(74) *Attorney, Agent, or Firm*—Townsend and Townsend and Crew

(57) ABSTRACT

The present invention provides methods for the amplifica-tion of nucleic acid molecules. Methods for amplifying target polynucleotides, including mRNA, using oligonucleotides, DNA and RNA polymerases are provided. The invention further provides compositions and kits for practicing the methods, as well as methods which use the amplification products.

32 Claims, 8 Drawing Sheets

OTHER PUBLICATIONS

Patanjali et al. "Construction of a Uniform–Abundance (Normalized) cDNA Library" Proc. Natl. Acad. Sci. USA 88:1943–1947 (1991).

Simone et al. "Sensitive Immunoassay of Tissue Cell Proteins Procured by Laser Capture Microdissection"American Journal of Pathology 156(2):445–452 (2000).

Van Gelder et al. "Amplified RNA Synthesized from Limited Quantities of Heterogeneous cDNA" Proc. Natl. Acad. Sci. USA 87:1663–1667 (1990).

Varmus. "Retroviruses" Science 240:1427–1435 (1988).

Weissman. "Molecular Genetic Techniques for Mapping the Human Genome" Mol. Biol. Med. 4:133–143 (1987).

Winslow et al. "Polyinosinic Acid as a Carrier in the Microscale Purification of Total RNA" Nucleic Acids Research 19(12):3251–3253 (1991).

Wu et al. "The Litigation Amplification Reaction (LAR)–Amplification of Specific DNA Sequences Using Sequential Rounds of Template–Dependent Litigation" Genomics 4:560–569 (1989).

* cited by examiner

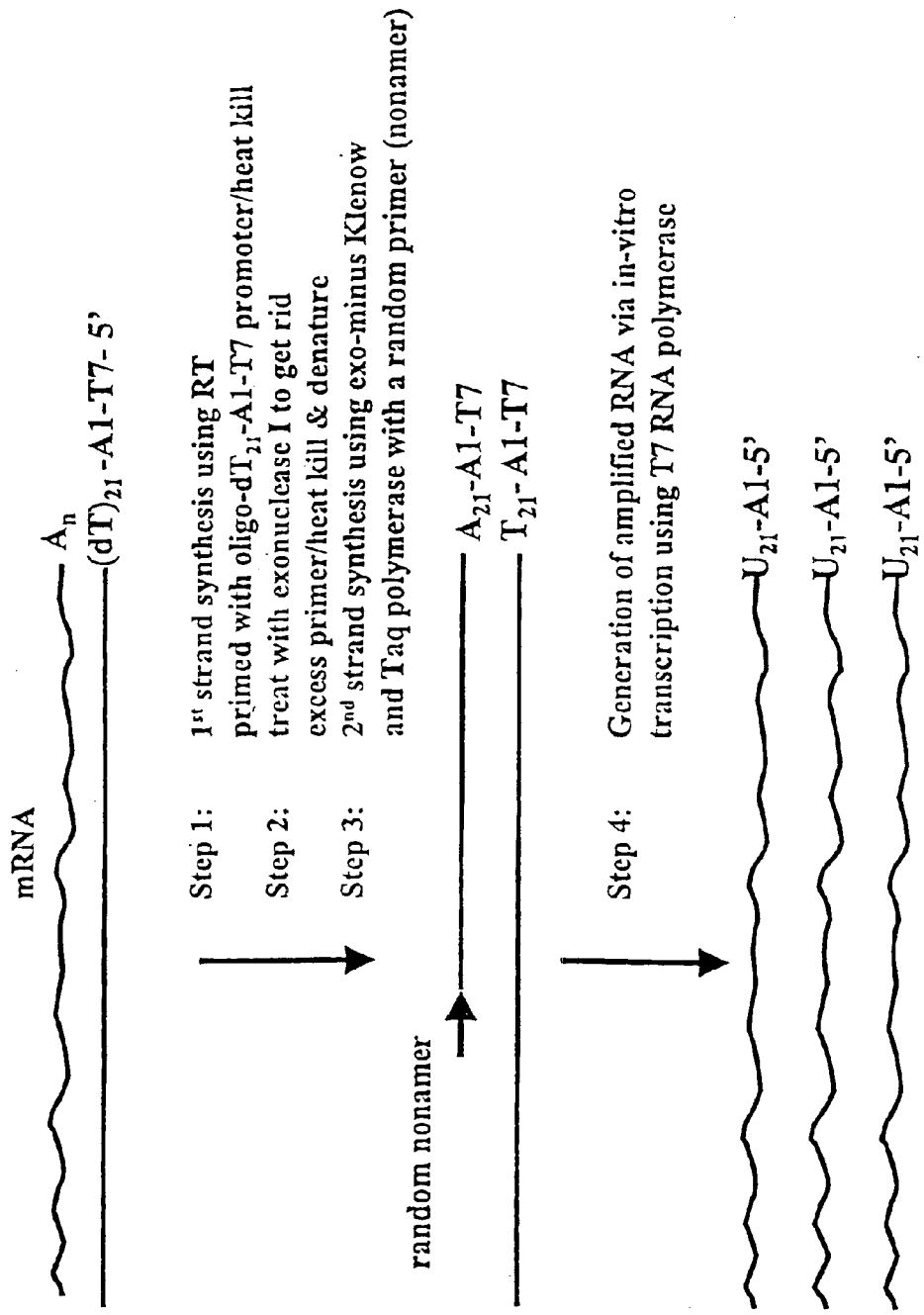

ROUND TWO:

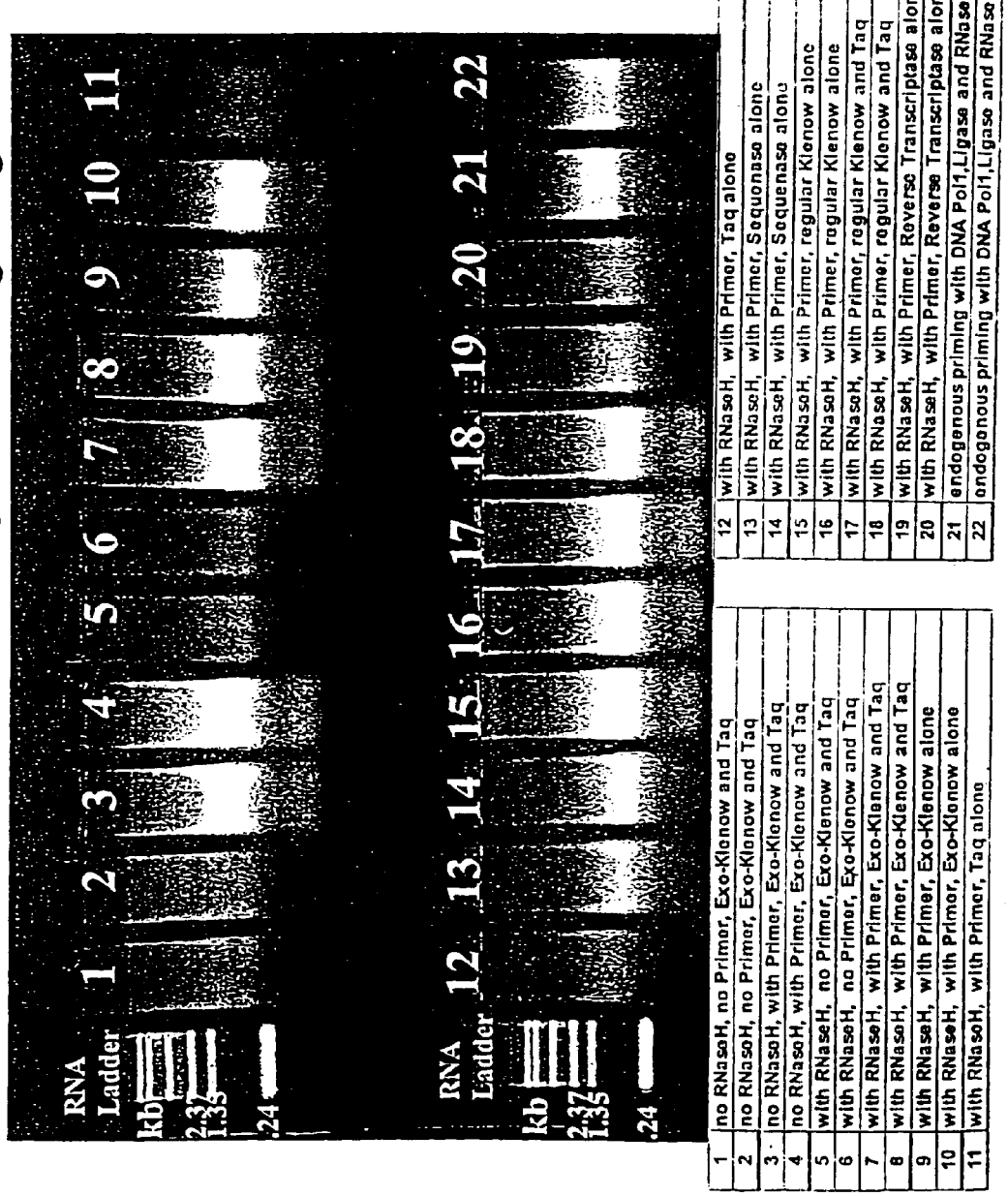
Figure 2A: Optimization of 2nd Strand Synthesis using Exogenous Primers

Figure 2B: Yields From Exogenous Priming of 2nd Strand Synthesis Using Different Enzymes

| SAMPLES | Condition Tested | ug of amplified RNA |
|---|---|---|
| 1 | no RNaseH, no Primer, Exo-Klenow and Taq | 3.6 |
| 2 |  | 3.4 |
| 3 | no RNaseH, with Primer, Exo-Klenow and Taq | 15.5 |
| 4 |  | 19.2 |
| 5 | with RNaseH, no Primer, Exo-Klenow and Taq | 3.4 |
| 6 |  | 3.0 |
| 7 | with RNaseH, with Primer, Exo-Klenow and Taq | 16.9 |
| 8 |  | 17.5 |
| 9 | with RNaseH, with Primer, Exo-Klenow alone | 18.7 |
| 10 |  | 16.8 |
| 11 | with RNaseH, with Primer, Taq alone | 2.8 |
| 12 |  | 3.6 |
| 13 | with RNaseH, with Primer, Sequenase alone | 9.0 |
| 14 |  | 10.4 |
| 15 | with RNaseH, with Primer, regular Klenow alone | 16.0 |
| 16 |  | 15.2 |
| 17 | with RNaseH, with Primer, regular Klenow and Taq | 13.7 |
| 18 |  | 15.2 |
| 19 | with RNaseH, with Primer, Reverse Transcriptase alone | 7.2 |
| 20 |  | 6.5 |
| 21 Eberwine1 | endogenous priming method with DNA Pol1, Ligase and RNaseH | 10.2 |
| 22 Eberwine2 |  | 11.7 |

| SAMPLES | Condition Tested | ave (ug) | fold diff vs GH | est. fold amp* |
|---|---|---|---|---|
| | Figure 2C: Comparison of Yields and Fold Amplification | | | |
| 1 | no RNaseH, no Primer, Exo-Klenow and Taq | 3.5 | 0.3 | 174 |
| 2 | | | | |
| 3 | no RNaseH, with Primer, Exo-Klenow and Taq | 17.3 | 1.6 | 865 |
| 4 | | | | |
| 5 | with RNaseH, no Primer, Exo-Klenow and Taq | 3.2 | 0.3 | 159 |
| 6 | | | | |
| 7 | with RNaseH, with Primer, Exo-Klenow and Taq | 17.2 | 1.6 | 862 |
| 8 | | | | |
| 9 | with RNaseH, with Primer, Exo-Klenow alone | 17.7 | 1.6 | 887 |
| 10 | | | | |
| 11 | with RNaseH, with Primer, Taq alone | 3.2 | 0.3 | 161 |
| 12 | | | | |
| 13 | with RNaseH, with Primer, Sequenase alone | 9.7 | 0.9 | 486 |
| 14 | | | | |
| 15 | with RNaseH, with Primer, regular Klenow alone | 15.6 | 1.4 | 778 |
| 16 | | | | |
| 17 | with RNaseH, with Primer, regular Klenow and Taq | 14.4 | 1.3 | 721 |
| 18 | | | | |
| 19 | with RNaseH, with Primer, Reverse Transcriptase alone | 6.8 | 0.6 | 342 |
| 20 | | | | |
| 21 Eberwine1 | endogenous priming method with DNA Pol1,Ligase and RNaseH | 11.0 | 1.0 | 548 |
| 22 Eberwine2 | | | | |

*fold-amplification calculated as follows: (final µg yield)/(0.020 µg) where 0.020 µg is an estimate based on the assumption that 2% of 1 µg of total RNA (the amount of starting material) is poly(A) RNA

Figure 3B:

| Total RNA | | | conc (ng/ml) | yield |
|---|---|---|---|---|
| 10 ng | 1 | Eberwine method | 1860 | 101.0 |
| 10 ng | 2 | Eberwine method | 1800 | 97.4 |
| 2 ng | 3 | Eberwine method | 448 | 26.9 |
| 2 ng | 4 | Eberwine method | 439 | 26.3 |
| 10 ng | 5 | exo-klenow + taq with t7a1 | 946 | 46.2 |
| 10 ng | 6 | exo-klenow + taq with t7a1 | 945 | 46.1 |
| 2 ng | 7 | exo-klenow + taq with t7a1 | 518 | 20.5 |
| 2 ng | 8 | exo-klenow + taq with t7a1 | 464 | 17.2 |
| 10 ng | 9 | exo-klenow + taq with t7a1dt | 1700 | 91.4 |
| 10 ng | 10 | exo-klenow + taq with t7a1dt | 1825 | 98.9 |
| 2 ng | 11 | exo-klenow + taq with t7a1dt | 2400 | 144.0 |
| 2 ng | 12 | exo-klenow + taq with t7a1dt | 648 | 38.9 |
| 10 ng | 13 | regular klenow + taq with t7a1 | 780 | 36.2 |
| 10 ng | 14 | regular klenow + taq with t7a1 | 808 | 37.9 |
| 2 ng | 15 | regular klenow + taq with t7a1 | 313 | 8.2 |
| 2 ng | 16 | regular klenow + taq with t7a1 | 298 | 7.3 |

SEQUENCE LISTING

<160> NUMBER OF SEQ ID NOS: 1

<210> SEQ ID NO 1
<211> LENGTH: 43
<212> TYPE: DNA
<213> ORGANISM: Artificial Sequence
<220> FEATURE:
<223> OTHER INFORMATION: Part of the M13 forward priming site

<400> SEQUENCE: 1
aaacgacggc cactgaattg taatacgact cactataggg aga          43

NUCLEIC ACID AMPLIFICATION

CROSS-REFERENCE TO RELATED APPLICATIONS

This application claims benefit of priority from U.S. Provisional Applications bearing Ser. No. 60/298,847, filed Jun. 15, 2001, and 60/257,801, filed Dec. 22, 2000, both of which are hereby incorporated by reference as if fully set forth.

TECHNICAL FIELD OF THE INVENTION

The technical field of this invention is enzymatic amplification of nucleic acids. More particularly, the invention provides methods, compositions and kits relating to amplifying (i.e., making multiple copies of) target polynucleotides to produce multiple copies thereof. The multiple copies may contain either the sense or antisense sequence of the amplified target polynucleotide. The invention also provides amplification of target polynucleotides, even if present in limited quantities, for use in subsequent analytical or preparative purposes.

BACKGROUND

Differential expression analysis of mRNA species in a test population requires the quantitative determination of different mRNA levels in the population. Although detection of a nucleic acid and its sequence analysis can be carried out by probe hybridization, the method generally lacks sensitivity when amounts of target nucleic acid in the test sample are low. Low copy number nucleic acid targets are difficult to detect even when using highly sensitive reporter groups like enzymes, fluorophores and radioisotopes. Detection of rare mRNA species is also complicated by factors such as heterogeneous cell populations, paucity of material, and the limits of detection of the assay method. Methods which amplify heterogeneous populations of mRNA also raise concerns with introduction of significant changes in the relative amounts of different mRNA species.

Applications of nucleic acid amplification method include detection of rare cells, pathogens, altered gene expression in malignancy, and the like. Nucleic acid amplification is potentially useful for both qualitative analysis, such as the detection of nucleic acids present in low levels, as well as the quantification of expressed genes. The latter is particularly useful for assessment of pathogenic sequences as well as for the determination of gene multiplication or deletion associated with malignant cell transformation. A number of methods for the amplification of nucleic acids have been described, e.g., exponential amplification, linked linear amplification, ligation-based amplification, and transcription-based amplification. An example of exponential nucleic acid amplification method is polymerase chain reaction (PCR) which has been disclosed in numerous publications. (see Mullis et al. *Cold Spring Harbor Symp. Quant. Biol.* 51:263–273 (1986); PCR Cloning Protocols: From Molecular Cloning to Genetic Engineering, Methods in Molecular Biology, White, B. A., ed., vol. 67 (1998); Mullis EP 201,184; Mullis et al., U.S. Pat. Nos. 4,582,788 and 4,683,195; Erlich et al., EP 50,424, EP 84,796, EP 258,017, EP 237,362; and Saiki R. et al., U.S. Pat. No. 4,683,194). Linked linear amplification is disclosed by Wallace et al. in U.S. Pat. No. 6,027,923. Examples of ligation-based amplification are the ligation amplification reaction (LAR), disclosed by Wu et al. in *Genomics* 4:560 (1989) and the ligase chain reaction, disclosed in EP Application No. 0320308 B1. Hampson et al. (Nucl. Acids Res. 24(23):4832–4835, 1996) describe a directional random oligonucleotide primed (DROP) method for use as part of global PCR amplification.

Isothermal target amplification methods include transcription-based amplification methods, in which an RNA polymerase promoter sequence is incorporated into primer extension products at an early stage of the amplification (WO 89/01050), and a target sequence or its complement is amplified by transcription and digestion of the RNA strand in a DNA/RNA hybrid intermediate. (See, for example, U.S. Pat. Nos. 5,169,766 and 4,786,600). These methods include transcription mediated amplification (TMA), self-sustained sequence replication (3SR), Nucleic Acid Sequence Based Amplification (NASBA), and variations thereof. (See Guatelli et al. *Proc. NatL Acad. Sci. U.S.A.* 87:1874–1878 (1990); U.S. Pat. Nos. 5,766,849 (TMA); and 5,654,142 (NASBA)).

Some transcription-based amplification methods (Malek et al., U.S. Pat. No. 5,130,238; Kacian and Fultz, U.S. Pat. No. 5,399,491; Burg et al., U.S. Pat. No. 5,437,990) use primer-dependent nucleic acid synthesis to generate a DNA or RNA product, which serves as a template for additional rounds of primer-dependent nucleic acid synthesis. These methods use at least two primers each having sequences complementary to different strands of a target nucleic acid sequence and results in an exponential amplification of the number of copies of the target sequence. However, these methods are not amenable for global gene expression monitoring applications.

Amplification methods that utilize a single primer are also useful for amplification of heterogeneous mRNA populations. Since the vast majority of mRNAs comprise a homopolymer of 20–250 adenosine residues on their 3' ends (the poly-A tail), poly-dT primers can be used for cDNA synthesis. "Single-primer amplification" protocols utilize a single primer containing an RNA polymerase promoter sequence and a sequence, such as oligo-dT, complementary to the 3'-end of the desired nucleic acid target sequence(s) ("promoter-primer"). (Kacian et al., U.S. Pat. No. 5,554,516; van Gelder et al., U.S. Pat. Nos. 5,545,522 ('522), 5,716,785 ('785) and 5,891,636 ('636)). These methods use, or could be adapted to use, a primer containing poly-dT for amplification of heterogeneous mRNA populations. In methods described in '522, '785 and '636, the promoter-primer is used to prime the synthesis of a first strand and an endogenously derived primer is used for second strand synthesis. The double-stranded cDNA thus generated includes a promoter coupled to a sequence corresponding to the target RNA and is used as a template for the synthesis of multiple copies of RNA complementary to the target sequence(s) ("antisense RNA") by use of RNA polymerase. The method described in U.S. Pat. No. 5,716,785 has been used to amplify cellular mRNA for monitoring gene expression (e.g., van Gelder et al. (1990), Proc. Natl. Acad. Sci. USA 87, 1663; Lockhart et al. (1996), Nature Biotechnol. 14, 1675).

Another method to produce "antisense RNA" with an RNA polymerase is disclosed by Loewy (U.S. Pat. No. 5,914,229) where a single-stranded nucleic acid of interest is combined with an oligonucleotide containing a double stranded promoter and a single stranded segment complementary to the nucleic acid of interest. Eberwine (BioTechniques 20:584–591 (1996)) disclose yet another means to amplify mRNA and produce "antisense RNA" by using immobilized oligo(dT)-T7 primers to produce the necessary cDNA. Wang et al. (U.S. Pat. No. 5,932,541) disclose the use of a "captureable" primer to produce the first strand of a cDNA before it is immobilized on a solid support (via the "capturable primer) prior to the synthesis of the second cDNA strand.

Another in vitro transcription protocol is disclosed by Hughes et al. (Nature Biotech. 19:342–347, April 2001), where a two primer system (modified from U.S. Pat. No. 6,132,997) and an adapted PCR coupled system are used.

SUMMARY OF THE INVENTION

The present invention provides methods, compositions and kits relating to amplifying target polynucleotides and generating amplified RNA (aRNA). Optionally, each aRNA contains known, or "anchor", sequences at the 5' and/or 3' ends. Anchor sequences may be used for the following: to generate sense amplified RNA and/or antisense amplified RNA (given RNAs that are flanked by T7 and T3 promoter sequences), to enhance second strand synthesis in the second round, and as primer sites for PCR amplification of normalized cDNA (see example 2 below). The aRNA may be in the form of either a "sense" RNA molecule containing all or part of the sequence found in the target polynucleotide, or an "antisense" RNA molecule containing a sequence complementary to all or part of the sequence found in the target polynucleotide, and may also include the optional anchor sequences.

In one aspect of the invention, a double stranded DNA molecule is produced to contain all or part of the sequence of the target polynucleotide of interest as well as one or more promoters capable of initiating the transcription of either strand of the double stranded DNA. The production of the double stranded DNA begins with the initial production of a first strand, "antisense" DNA by hybridizing a strand of the target polynucleotide with a first oligonucleotide comprising a first primer region containing a sequence complementary to a sequence at or near the 3' end of the target polynucleotide and a RNA polymerase promoter region coupled to the 5' end of the first primer region. If the target polynucleotide is single stranded, it may be used directly. If the target polynucleotide is double stranded, it is first denatured to generate a single stranded target polynucleotide. The single stranded target polynucleotide is used as the template for the production of said first strand DNA. Optionally, the first primer region and the promoter region is separated by a known, or "anchor", sequence. Moreover, the promoter region is optionally relatively unhybridizable to the polynucleotide template.

After said hybridizing event, a first strand DNA complementary to the target polynucleotide is produced by extending the first oligonucleotide. Where the target polynucleotide used as the template is a single stranded RNA molecule, enzymatic extension of the first oligonucleotide with reverse transcriptase activity may be used. As an optional, but preferred embodiment of the invention, excess or residual first oligonucleotides not used to prime first strand DNA molecules are degraded. After production of the first strand DNA, it is separated from the target polynucleotide template, and one or more second oligonucleotides are hybridized to the first strand DNA. This may be accomplished by a heating step that also terminates reverse transcriptase activity.

The one or more second oligonucleotide contain a second primer region containing sequences which are complementary to all or part of the first strand DNA to permit hybridization to occur. The second primer regions may contain, or be, random sequences of various lengths, such that hybridization may occur at various sequences along the length of the first strand DNA. Alternatively, the second primer regions may contain one or more known sequences, complementary to sequences on the first strand DNA, such that the one or more second oligonucleotides will hybridize at known positions along the first strand DNA. Preferably, the known sequences used in the second primer region are complementary to a sequence at or near the 3' end of the first strand DNA or at least located at some distance from the 5' end of the first strand DNA.

The second oligonucleotide may optionally further contain a second known, or "anchor", sequence coupled to the 5' end of the second primer region. In another optional embodiment of the second oligonucleotide, a second promoter may be coupled either to the 5' end of the second primer region or to the 5' end of the "anchor" sequence.

After hybridization of the second oligonucleotide, a double stranded DNA is produced by forming a second strand DNA, by primer extension, that is complementary to all or part of the first strand DNA. Due to the first strand DNA being produced via the use of a promoter-containing first oligonucleotide, the resultant double stranded DNA has a promoter region coupled to an end of the double stranded DNA corresponding to the 5' end of the first strand DNA. The first oligonucleotide is preferably designed to permit the promoter region to initiate transcription that produces RNA containing all or part of the first primer region and any optional "anchor" sequence present in the first oligonucleotide.

In another aspect of the invention, and after production of the double stranded DNA, the promoter is contacted with an RNA polymerase capable of initiating transcription from the promoter to transcribe one or more copies of an amplified RNA (aRNA) complementary to sequences present on the second strand DNA. Preferably, the aRNA comprises in a 5' to 3' order, the optionally present "anchor" sequence, the first primer sequence, a sequence complementary to all or part of the target polynucleotide, and a sequence complementary to the second oligonucleotide. The resultant aRNA would thus be "antisense" relative to the target polynucleotide of interest.

The above discussion may also be viewed as "round one" of the nucleic acid amplification provided by the present invention.

In another aspect of the invention, "round two" amplification is provided to enable further amplification of "antisense" aRNA as well as "sense" aRNA. Round two amplification is possible by using the above aRNA to produce multiple copies of double stranded DNA constructs to further amplify the target polynucleotide. In round two, the above aRNA is used to first produce another first strand DNA. This starts by hybridizing the above aRNA to one or more "round one" second oligonucleotides as described above. This round two first strand DNA is produced upon extension of the second oligonucleotide(s) with reverse transcriptase activity, with the above aRNA acting as the template. After production of the round two first strand DNA, it is separated from the aRNA template and hybridized with the "round one" first oligonucleotide as described above. Extension of the first oligonucleotide produces a round two second strand DNA, and simultaneous extension of the round two first strand DNA at its 3' end, to be fully complementary to the first oligonucleotide, results in the round two double stranded DNA molecule. This round two double stranded DNA molecule contains a promoter region, present via the first oligonucleotide, that is coupled to an end corresponding to the 5' end of the round two second strand DNA. Thus initiation of transcription from the promoter region results in production of one or more copies of round two aRNA, which contain sequences of the "round one" aRNA. Preferably, this round two aRNA comprises in a 5' to 3' order, the optionally present "anchor" sequence and the first primer sequence (from the "round one" first oligonucleotide), a sequence complementary to all or part of the original target polynucleotide, and a sequence complementary to the second oligonucleotide(s) used. The resultant aRNA would again be "antisense" relative to the original target polynucleotide of interest.

Use of round two permits significant further amplification of the target polynucleotide because the quantity of "round one" aRNA is used to prepare multiple round two double stranded DNAs which may then used to produce even larger amounts of aRNA upon transcription.

In further embodiments of round two, the second oligonucleotide(s) used to generate the round two first strand DNA can be used to affect the form of round two aRNA. In one embodiment, and consistent with its description in "round one", the second oligonucleotides contain second primer regions containing random sequences such that the second oligonucleotide hybridizes to various sequences along the length of the "round one" aRNA. As such, the resultant double stranded DNA permits round two transcription to produce aRNA containing all or part, depending on where hybridization occurs, of the sequences of the "round one" aRNA that are complementary to the original target polynucleotide. Of course the second oligonucleotide may still optionally contain "anchor" sequences linked to the 5' end.

In another embodiment of round two, the second oligonucleotide(s) contain second primer regions that contain one or more known sequences, complementary to sequences on the "round one" aRNA. Thus, the second oligonucleotide(s) will hybridize at known position(s) along the aRNA. If hybridization occurs at the 3' end of the aRNA, then the resultant double stranded DNA permits round two transcription to produce aRNA identical to "round one" aRNA. If the second oligonucleotide(s) hybridize internally within the aRNA template, the resultant double stranded DNA permits round two transcription to produce aRNA containing part of the sequences of the "round one" aRNA that are complementary to the original target polynucleotide. Of course the second oligonucleotide may still optionally contain "anchor" sequences linked to the 5' end.

In both of the above embodiments of round two, the second oligonucleotide(s) used may, as described for "round one", optionally contain a promoter region directly or indirectly coupled to the 5' end of the second primer region. Extension of the second oligonucleotide, followed by priming and extension with the "round one" first oligonucleotide, results in a double stranded DNA molecule wherein both strands can serve as a template for transcription initiated from either the promoter coupled to the second oligonucleotide and/or the promoter coupled to the "round one" first oligonucleotide. This possible embodiment permits additional alternatives for the practice of round two.

In one alternative embodiment, the promoter region present in the second oligonucleotide(s) is different from the promoter present in the first oligonucleotide (of round one or round two). This results in the double stranded DNA containing promoter regions at both ends of the molecule, such that initiation of transcription from the promoter region present via the first oligonucleotide results in the production of aRNA complementary (or "antisense") to the original target polynucleotide, while initiation of transcription from the promoter region present via the second oligonucleotide results in the production of aRNA containing sequences of the original target polynucleotide. The latter aRNA are thus "sense" relative to the original target polynucleotide.

In a further alternative embodiment of round two, a slightly different double stranded DNA is produced. This starts by hybridizing "round one" aRNA with a second oligonucleotide (as described for "round one") that contains a promoter region as described above. After production of the round two first strand DNA and separation away from the aRNA template, the round two first strand DNA is hybridized with an oligonucleotide which does not contain a promoter region. As such, the round two second strand DNA may be produced by extension of an oligonucleotide as described above for the "round one" first oligonucleotide except that it does not contain a promoter region or instead of this "round one" first oligonucleotide that is promoter-less, one could use a random primer for subsequent extension. Extension to produce the round two second strand DNA includes a sequence complementary to the primer region (containing the promoter region) of the second oligonucleotide and this occurs simultaneously with the extension of the round two first strand DNA at its 3' end to be fully complementary to the promoterfree oligonucleotide primer. The resultant round two double stranded DNA molecule would thus only contain a promoter region, present via the second oligonucleotide used for extension of the first strand DNA, that is coupled to an end corresponding to the 5' end of the round two first strand DNA. Thus initiation of transcription from the promoter region results in production of one or more copies of round two aRNA which contain sequences complementary to all or part of "round one" aRNA. Stated differently, this type of round two aRNA would contain all or part of the sequences of the original target polynucleotide. As such, the aRNA is "sense" relative to the original target polynucleotide. Preferably, this type of round two aRNA comprises in a 5' to 3' order, the optionally present "anchor" sequence and the second primer sequence from the round two second oligonucleotide, the sequence of all or part of the original target polynucleotide, and a sequence complementary to the promoterfree oligonucleotide used.

It should be noted that in all of the above methods, "exogenous primers" are present at least in the form of the oligonucleotides used to prime synthesis of the second DNA strand in "round one" or the first DNA strand in round two.

The methods of the present invention may be used to detect a RNA molecule of interest from a cell or organism. Preferably the cell is a eukaryotic or human cell, more preferred are cells from malignant cells, such as those associated with cancer, especially breast cancer. The present methods may be used to amplify one mRNA from the entire population of mRNAs in a given cell/tissue/organism. In preferred embodiments of the invention, the entire mRNA population from one or more than one cell that is laser-captured (laser capture microdissection) from fixed tissues from model organisms of human diseases or actual human tissue (postmortem or biopsy material) is amplified. More than one cell includes a plurality or other multitude of cells, from a cell culture or a tissue or cell type therein. Cells that may be used in the practice of the present invention include, but are not limited to, primary cells, cultured cells, tumor cells, non-tumor cells, blood cells, cells of the the pituitary or other endocrine glands, bone cells, lymph node cells, brain cells, lung cells, heart cells, spleen cells, liver cells, kidney cells, and vascular tissue cells.

Beyond cancer cells, the present invention may be applied to tissues (and cell types therein) involved in, or associated with, any disease or undesired condition. For example, and without limiting the invention, the present invention may be used to determine gene expression in neuronal and non-neuronal cells involved in disorders of the nervous system, such as, but not limited to, neurodegenerative diseases, including Parkinson's disease and Alzheimer's disease; multiple sclerosis; and psychiatric disorders, including schizophrenia and affective disorders such as manic depression, lack of apetitite control, and attention deficit disorder. Expressed nucleic acids from different neuronal cell types involved in or associated with the above disorders, either by single or multiple cells of the same type or subtype, may be amplified with the present invention for further characterization. Similarly, expressed nucleic acids from non-neuronal cells associated with such disorders (including, but not limited to microglial cells, astrocytes, oligodendricytes, and infiltrating inflammatory cells) may also be amplified with the present invention.

Also without limiting the invention, expressed nucleic acids from cells associated with disorders of the cardiovascular and urinary systems may be amplified with the present invention. Examples from the area of cardiovascular disease include, but are not limited to, smooth muscle cells, endothelial cells and macrophages while examples from kidney disorders include, but are not limited to, cells of the cortex, medulla, glomerulus, proximal and distal tubules, Bowman's capsule and the Loop of Henley.

Inflammatory and autoimmune diseases are additional non-limiting examples of disorders wherein the tissues and cells involved in or associated therewith may be used in combination with the present invention. Examples of such disorders include rheumatoid arthritis, myasthenia gravis, lupus erythematosus, certain types of anemia, multiple sclerosis, and juvenile-onset diabetes. Cells involved in such diseases include neutrophils, eosinophils, basophils, monocytes, macrophages, lymphocytes, Additional examples of cancer cells which may be used in conjunction with the present invention include, but are not limited to, cells from sarcomas, carcinomas, lymphomas, leukemias, prostate cancer, lung cancer, colorectal cancer, soft tissue cancers, biopsies, skin cancer, brain cancer, liver cancer, ovarian cancer, and pancreatic cancer. Kits containing one or more components, such as the primers or polymerases of the invention, optionally with an identifying description or label or instructions relating to their use in the methods of the present invention are also provided by the present invention.

BRIEF DESCRIPTION OF THE DRAWINGS

FIGS. 1A through 1C illustrate one exemplary embodiment using a single stranded RNA as the target polynucleotide. Generally, RT refers to reverse transcriptase; heat kill refers to termination of RT activity; exonuclease treatment is an optional additional step to remove excess primer; and denaturation refers to the separation of the first strand DNA from the target polynucleotide. With respect to "round one", the use of random nonamers, exonuclease minus Klenow and Taq polymerase (thermal stable DNA polymerase from Thermus aquaticus), a T7 promoter, and an optional Al "anchor" sequence reflect just one possible embodiment of the invention. With respect to "round two modified", the use of a T3 promoter containing primer reflects just one possible embodiment of the invention.

FIGS. 2A–2C show the results of a test comparing the synthesis of "round one" second strand in accordance with different embodiments of the invention as well as comparison to "endogenous priming" conditions without the use of exogenous primers. FIG. 2A shows the results of gel electrophoresis analysis of aRNA via different second strand syntheses. Each set of conditions was conducted in duplicate. FIG. 2B shows the yields of amplified RNA (aRNA) for each of the conditions tested. FIG. 2C shows a comparison of the yields with the fold amplification.

FIGS. 3A and 3B show the successful results of amplifying small amounts of total RNA (2 ng and 10 ng of total RNA extracted from mouse brain). These results demonstrate that very small quantities of mRNA can be amplified.

DETAILED DESCRIPTION OF THE INVENTION

A. Definitions

Figure 1B:
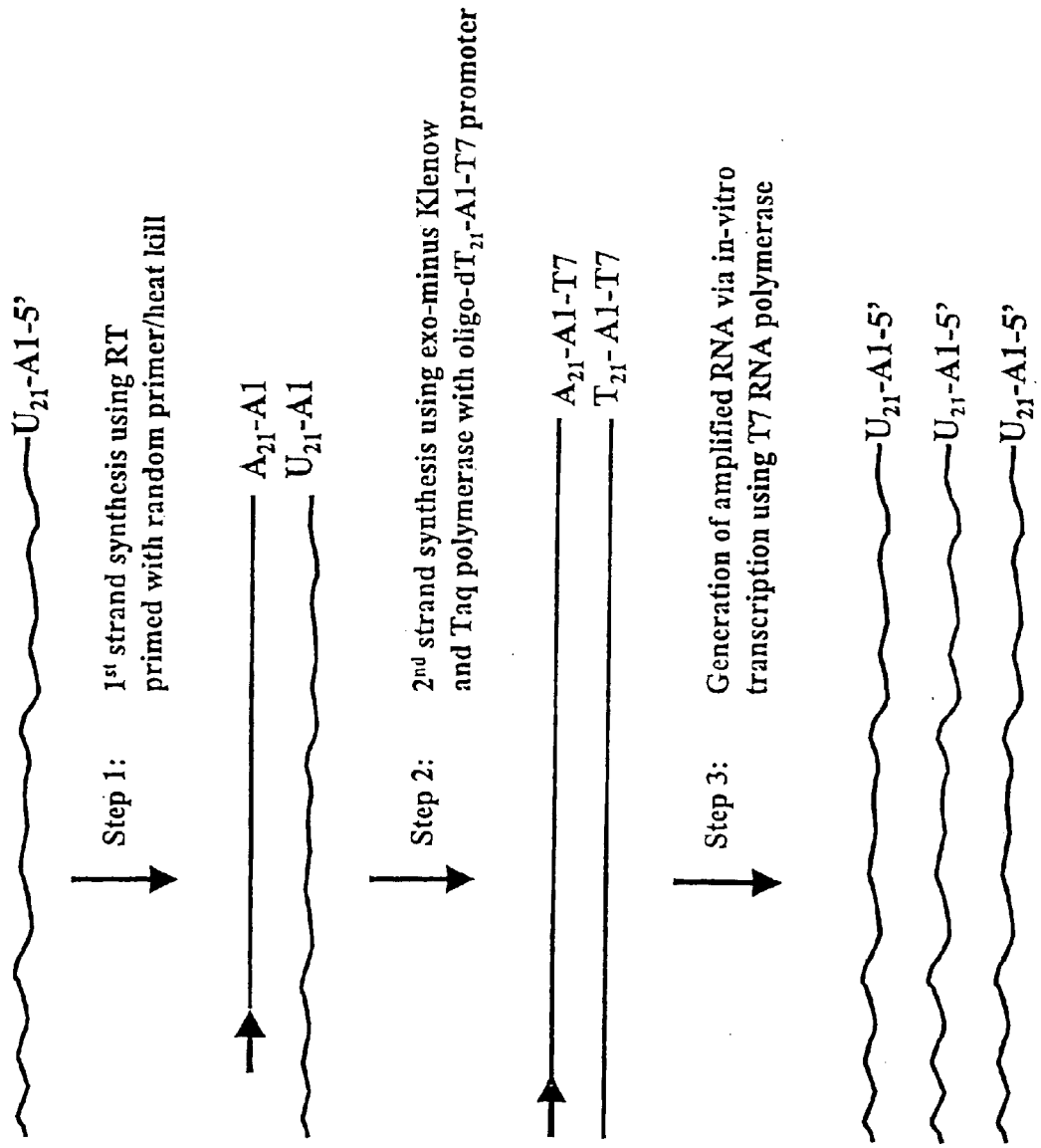

A "polynucleotide" is a polymeric form of nucleotides of any length, either ribonucleotides or deoxyribonucleotides. This term refers only to the primary structure of the molecule. Thus, this term includes double- and single-stranded DNA and RNA. It also includes known types of modifications including labels known in the art, methylation, "caps", substitution of one or more of the naturally occurring nucleotides with an analog, and internucleotide modifications such as uncharged linkages (e.g., phosphorothioates, phosphorodithioates, etc.), appendant moieties (including proteins such as nucleases, toxins, antibodies, signal peptides, poly-L-lysine, etc.), intercalators (e.g., acridine, psoralen, etc.), chelators (e.g., metals, radioactive metals, etc.), alkylators, modified linkages (e.g., alpha anomeric nucleic acids, etc.), as well as unmodified forms of the polynucleotide.

A "target polynucleotide" or "target sequence," as used herein, contains a polynucleotide sequence of interest, for which amplification is desired. The target sequence may be known or not known, in terms of its actual sequence. Generally, a "template," as used herein, is a polynucleotide that contains the target polynucleotide sequence. In some instances, the terms "target sequence," "template DNA," "template polynucleotide," "target nucleic acid," "target polynucleotide," and variations thereof, are used interchangeably.

The primer regions containing known sequences, as used herein, are selected to be "substantially" complementary to each specific sequence to be amplified, i.e.; the primers should be sufficiently complementary to hybridize to their respective targets. Therefore, the primer sequence need not reflect the exact sequence of the target, and can, in fact be "degenerate." Non-complementary bases or longer sequences can be interspersed into the primer, provided that the primer sequence has sufficient complementarity with the sequence of the target to be amplified to permit hybridization and extension.

Primer regions containing random sequences, as used herein, are not necessarily known to be complementary to target sequences to be amplified, but preferably include sequences that are sufficiently complementary to target sequences to permit primer extension reactions to occur via polymerase activity. Primers may be of any length suitable for hybridization and primer extension under the conditions used. As noted above, primers may be random such that they contain heterologous sequences. Primers heterologous in lengths may also be used in the practice of the invention. Primers may be DNA, RNA or a chimeric combination thereof in structure. Preferred random primer lengths are from about four nucleotides to about 10 nucleotides. Even more preferred are random primers of nine or about nine nucleotides in length. Primers of known sequences may be of lengths from about 12 to about 50 to 100 nucleotides in length. The term "amplify" is used in the broad sense to mean creating an amplification product which may include, for example, additional target molecules, or target-like molecules or molecules complementary to the target molecule, which molecules are created by virtue of the presence of the target molecule in the sample. In the situation where the target is a nucleic acid, an amplification product can be made enzymatically with RNA polymerases with the involvement of DNA polymerases in generating double stranded DNA. "Amplification," as used herein, generally refers to the process of producing multiple copies of a desired sequence. "Multiple copies" mean at least 2 copies. A "copy" does not necessarily mean perfect sequence complementarity or identity to the template sequence. For example, copies can include nucleotide analogs such as deoxyinosine, intentional sequence alterations (such as sequence alterations introduced through a primer comprising a sequence that is hybridizable, but not complementary, to the template), and/ or sequence errors that occur during amplification.

The present invention also provides methods for amplifying mRNA. As such, the subject invention provides methods of producing amplified amounts of RNA from a starting target mRNA. By amplified amounts is meant that for each starting mRNA, multiple corresponding amplified RNAs (aRNAs) are produced where the amplified RNA has a sequence identical to or complementary to the initial mRNA. By corresponding is meant that the aRNA shares a substantial amount of sequence identity with the starting mRNA or its complement. Substantial amount means at least 95%, usually at least 98% and more usually at least 99%, and sequence identity is determined using the BLAST algorithm, as described in Altschul et al. (1990), J. Mol. Biol. 215:403–410 (using the published default setting, i.e. parameters w=4, t=17). Generally, the number of corresponding aRNA molecules produced for each starting mRNA during the linear amplification methods will be at least about 10, usually at least about 50 and more usually at least about 100, where the number may be as great as 600 or greater, but often does not exceed about 5000. Fold amplification of mRNAs by the present invention is from about 1000 fold per round to about 5000 fold per round. As used herein, the term "anchor" or "anchor sequence" refers to a specific nucleic acid sequence that may serve to identify a batch of polynucleotides containing said sequence therein. Polynucleotides from the same biological source are covalently "anchored" with a specific sequence so that in subsequent analysis the polynucleotide can be identified according to its source of origin. The sequence "anchors" may also serve as all or part of the primer regions as disclosed herein. Alternatively, the "anchors" may serve simply to link primer regions to promoter regions as disclosed herein. While the use of anchor sequences is fully within the scope of the present invention, an additional aspect of the invention is the unexpected discovery that the non-inclusion of an anchor sequence may result in improved production of cDNAs and aRNAs when compared to conditions including the use of an anchor sequence.

A "microarray" is a linear or two-dimensional array of preferably discrete regions, each having a defined area, formed on the surface of a solid support. The density of the discrete regions on a microarray is determined by the total numbers of target polynucleotides to be detected on the surface of a single solid phase support, preferably at least about 50/cn$^2$, more preferably at least about 100/cm$^2$, even more preferably at least about 500/cm$^2$, and still more preferably at least about 1,000/cm$^2$. As used herein, a DNA microarray is an array of oligonucleotide primers or cDNAs placed on a chip or other surfaces. Since the position of each particular group of primers or cDNAs in the array is known, the identities of the target polynucleotides can be determined based on their binding to a particular position in the microarray.

The term "label" refers to a composition capable of producing a detectable signal indicative of the presence of the target polynucleotide in an assay sample. Suitable labels include radioisotopes, nucleotide chromophores, enzymes, substrates, fluorescent molecules, chemiluminescent moieties, magnetic particles, bioluminescent moieties, and the like. As such, a label is any composition detectable by spectroscopic, photochemical, biochemical, immunochemical, electrical, optical or chemical means.

The term "support" refers to conventional supports such as beads, particles, dipsticks, fibers, filters, membranes and silane or silicate supports such as glass slides.

As used herein, a "biological sample" refers to a sample of tissue or fluid isolated from an individual, including but not limited to, for example, blood, plasma, serum, spinal fluid, lymph fluid, the external sections of the skin, respiratory, intestinal, and genitourinary tracts, tears, saliva, milk, cells (including but not limited to blood cells), tumors, organs, and also samples of in vitro cell culture constituents.

The term "biological sources" as used herein refers to the sources from which the target polynucleotides are derived. The source can be any form of "biological sample" as described above, including but not limited to, cell, tissue or fluid. "Different biological sources" can refer to different cells, tissues or organs of the same individual, or cells, tissues or organs from different individuals of the same species, or cells, tissues or organs from different species. The term may also refer to cells, especially human cells, such as those that are malignant or otherwise associated with cancer, especially breast cancer; and cells that are laser-captured (laser capture microdissection) from fixed tissues from model organisms of human diseases or actual human tissue (postmortem or biopsy material).

To "inhibit" is to decrease or reduce an activity, function, and/or amount as compared to a reference.

A "complex" is an assembly of components. A complex may or may not be stable and may be directly or indirectly detected. For example, as is described herein, given certain components of a reaction, and the type of product(s) of the reaction, existence of a complex can be inferred. For purposes of this invention, a complex is generally an intermediate with respect to the final amplification product(s).

A "portion" or "region," used interchangeably herein, of a polynucleotide or oligonucleotide is a contiguous sequence of 2 or more bases. In other embodiments, a region or portion is at least about any of 3, 5, 10, 15, 20, 25 contiguous nucleotides.

A region, portion, or sequence which is "adjacent" to another sequence directly abuts that region, portion, or sequence. For example, an RNA portion which is adjacent to a 5' DNA portion of a composite primer directly abuts that region.

A "reaction mixture" is an assemblage of components, which, under suitable conditions, react to form a complex (which may be an intermediate) and/or a product(s).

It must be noted that as used in this specification and the appended claims, the singular forms "a", "an" and "the" include corresponding plural references unless the context clearly dictates otherwise.

"Expression" includes transcription of a deoxyribonucleic acid and/or translation of a ribonucleic acid.

As used herein, the term "comprising" and its cognates are used in their inclusive sense; that is, equivalent to the term "including" and its corresponding cognates.

Conditions that "allow" an event to occur or conditions that are "suitable" for an event to occur, such as hybridization, strand extension, and the like, or "suitable" conditions are conditions that do not prevent such events from occurring. Thus, these conditions permit, enhance, facilitate, and/or are conducive to the event. Such conditions, known in the art and described herein, depend upon, for example, the nature of the nucleotide sequence, temperature, and buffer conditions. These conditions also depend on what event is desired, such as hybridization, cleavage, strand extension or transcription.

Sequence "mutation," as used herein, refers to any sequence alteration in a sequence of interest in comparison to a reference sequence. A reference sequence can be a wild type sequence or a sequence to which one wishes to compare a sequence of interest. A sequence mutation includes single nucleotide changes, or alterations of more than one nucleotide in a sequence, due to mechanisms such as substitution, deletion or insertion. Single nucleotide polymorphism (SNP) is also a sequence mutation as used herein.

The term "3'" (three prime) generally refers to a region or position in a polynucleotide or oligonucleotide 3' (downstream) from another region or position in the same polynucleotide or oligonucleotide.

The term "5'" (five prime) generally refers to a region or position in a polynucleotide or oligonucleotide 5' (upstream) from another region or position in the same polynucleotide or oligonucleotide.

The term "3'-DNA portion," "3'-DNA region," "3'-RNA portion," and "3'-RNA region," refer to the portion or region of a polynucleotide or oligonucleotide located towards the 3' end of the polynucleotide or oligonucleotide, and may or may not include the 3' most nucleotide(s) or moieties attached to the 3' most nucleotide of the same polynucleotide or oligonucleotide. The 3' most nucleotide(s) can be preferably from about 1 to about 20, more preferably from about 3 to about 18, even more preferably from about 5 to about 15 nucleotides.

The term "5'-DNA portion," "5'-DNA region," "5'-RNA portion," and "5'-RNA region," refer to the portion or region of a polynucleotide or oligonucleotide located towards the 5' end of the polynucleotide or oligonucleotide, and may or may not include the 5' most nucleotide(s) or moieties attached to the 5' most nucleotide of the same polynucleotide or oligonucleotide. The 5' most nucleotide(s) can be preferably from about 1 to about 20, more preferably from about 3 to about 18, even more preferably from about 5 to about 15 nucleotides.

"Detection" includes any means of detecting, including direct and indirect detection. For example, "detectably fewer" products may be observed directly or indirectly, and the term indicates any reduction (including no products). Similarly, "detectably more" product means any increase, whether observed directly or indirectly.

Unless defined otherwise all technical and scientific terms used herein have the same meaning as commonly understood to one of ordinary skill in the art to which this invention belongs.

B. General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., eds., 1994).

Primers, oligonucleotides and polynucleotides employed in the present invention can be generated using standard techniques known in the art.

While the present invention may be most commonly practiced in solution, all or part thereof may be practiced as part of a solid (or immobilized) or in situ state. For example, and without limiting the invention, synthesis of the first cDNA strand may be conducted in situ or with a first primer promoter oligonucleotide that is immobilized on a solid support (such as, but not limited to, a bead, or a membrane or the surface of a solid container).

C. Promoter-Primer Oligonucleotides

In some embodiments, the methods employ a promoter sequence for transcription which is provided by a promoter-primer oligonucleotide. A promoter-primer for use in the methods and compositions of the present invention is a single-stranded polynucleotide, generally DNA, comprising a promoter sequence that is designed for formation of a double stranded promoter of an RNA polymerase, and a portion capable of hybridizing to a template sequence, preferably at or near its 3' end. In one embodiment, the promoter sequence is located in the 5' portion of the oligonucleotide and the hybridizing sequence is located in the 3' portion of the oligonucleotide. In another embodiment, and typically, the promoter and hybridizing sequences are different sequences. In another possible embodiment, the promoter and hybridizing sequences overlap in sequence identity. In yet another embodiment, the promoter and hybridizing sequences are the same sequence, and thus are in the same location on the promoter-primer. In the embodiments wherein hybridization of the promoter-primer to a template results in a duplex comprising an overhang, DNA polymerase may be used to fill in the overhang to create a double stranded promoter capable of effecting transcription by a suitable RNA polymerase.

A number of RNA polymerase promoters may be used for the promoter region of the promoter-primer. Suitable promoter regions will be capable of initiating transcription from an operationally linked DNA sequence in the presence of ribonucleotides and an RNA polymerase under suitable conditions. The promoter region will usually comprise between about 15 and 250 nucleotides, preferably between about 17 and 60 nucleotides, from a naturally occurring RNA polymerase promoter, a consensus promoter region, or an artificial promoter region, as described in Alberts et al. (1989) in Molecular Biology of the Cell, 2d ed. (Garland Publishing, Inc.). In general, prokaryotic promoters are preferred over eukaryotic promoters, and phage or virus promoters are most preferred. As used herein, the term "operably linked" refers to a functional linkage between the affecting sequence (typically a promoter) and the controlled sequence (the mRNA binding site). The promoter sequence can be from a prokaryotic or eukaryotic source. Representative promoter regions of particular interest include T7, T3 and SP6 as described in Chamberlin and Ryan, The Enzymes (ed. P. Boyer, Academic Press, New York) (1982) pp 87–108. In a preferred embodiment, the RNA polymerase promoter sequence is a T7 RNA polymerase promoter sequence comprising at least nucleotides −17 to +6 of a wildtype T7 RNA polymerase promoter sequence, preferably joined to at least 20, preferably at least 30 nucleotides of upstream flanking sequence, particularly upstream T7 RNA polymerase promoter flanking sequence. Additional downstream flanking sequence, particularly downstream T7 RNA polymerase promoter flanking sequence, e.g. nucleotides +7 to +10, may also be advantageously used. For example, in one particular embodiment, the promoter comprises nucleotides −50 to +10 of a natural class III T7 RNA polymerase promoter sequence.

In some embodiments, the promoter-primer comprises an intervening anchor sequence between a promoter sequence and a portion capable of hybridizing to the 3' end of a polynucleotide template. Suitable length of the intervening anchor sequence can be empirically determined, and can be at least about 1, 2, 4, 6, 8, 10, 12, 15 nucleotides. Suitable sequence identity of the intervening anchor sequence can also be empirically determined, and the sequence is designed to preferably, but not necessarily, enhance degree of amplification as compared to omission of the sequence. In one embodiment, the intervening sequence is a sequence that is designed to provide for enhanced, or more optimal, transcription by the RNA polymerase used. Generally, the sequence is not related (i.e., it does not substantially hybridize) to the target nucleic acid. More optimal transcription occurs when transcriptional activity of the polymerase from a promoter that is operatively linked to said sequence is greater than from a promoter that is not so linked. The sequence requirements within the actual promoter for optimal transcription are generally known in the art as previously described for various DNA dependent RNA polymerases, such as in U.S. Pat. Nos. 5,766,849 and 5,654,142, and can also be empirically determined.

The length of the portion of the promoter-primer that hybridizes to a template is preferably from about 5 to about 50 nucleotides, more preferably from about 10 to about 40 nucleotides, even more preferably from about 15 to about 35 nucleotides, and most preferably from about 20 to 30 nucleotides. In some embodiments, the hybridizing portion is at least about any of the following: 3, 5, 10, 15, 20; and less than about any of the following: 30, 40, 50, 60. The complementarity of the hybridizing portion is preferably at least about 25%, more preferably at least about 50%, even more preferably at least about 75%, and most preferably at least about 90% to 100%, to its intended binding sequence on the target nucleic acid. For the amplification of polyadenylated target polynucleotides, the primer portion is preferably poly dT of the lengths described above and below.

Primer, promoter-primer and anchor oligonucleotides described above and throughout this specification may be prepared using any suitable method, such as, for example, the known phosphotriester and phosphite triester methods, or automated embodiments thereof. Oligonucleotides of the invention can be synthesized by a number of approaches, e.g. Ozaki et at, Nucleic Acids Research, 20:5205–5214 (1992); Agarwal et at, Nucleic Acids Research, 18:5419–5423 (1990); or the like. The oligonucleotides of the invention may be conveniently synthesized on an automated DNA synthesizer, e.g. an Applied Biosystems, Inc. Foster City, Calif.) model 392 or 394 DNA/RNA Synthesizer, using standard chemistries, such as phosphoramidite chemistry, e.g. disclosed in the following references: Beaucage and Iyer, Tetrahedron, 48:2223–2311 (1992); Molko et al, U.S. Pat. Nos. 4,980,460; Koster et al, U.S. Pat. No. 4,725,677; Caruthers et al, U.S. Pat. Nos. 4,415,732; 4,458,066; and 4,973,679; and the like. Alternative chemistries, e.g. resulting in non-natural backbone groups, such as phosphorothioate, phosphoramidate, and the like, may also be employed provided that the hybridization efficiencies of the resulting oligonucleotides and/or cleavage efficiency of the exonuclease employed are not adversely affected. Preferably, the oligonucleotide is in the range of 20–100 nucleotides in length. More preferably, the oligonucleotide is in the range of 20–85 nucleotides in length. The precise sequence and length of an oligonucleotide of the invention depends in part on the nature of the target polynucleotide to which it binds. The binding location and length may be varied to achieve appropriate annealing and melting properties for a particular embodiment. Guidance for making design choices can be found in many of the above-cited references describing the "Taqman" type of assays. One method for synthesizing oligonucleotides on a modified solid support is described in U.S. Pat. No. 4,458,066. It is also possible to use a primer that has been isolated from a biological source (such as a restriction endonuclease digest of cloned genomic DNA).

In preferred embodiments of the invention, the molar ratio of primers to template sequences is from about 500:1 to about 8000:1. More preferred are molar ratios of about 1000:1, about 1500:1, about 1600:1, about 1700:1, about 1800:1, about 1900:1, about 2000:1, about 2500:1, about 3000:1, about 3500:1, about 4000:1, about 4500:1, about 5000:1, about 5500:1, about 6000:1, about 6500:1, about 7000:1, and about 7500:1. Most preferred are molar ratios of about 1100:1, about 1200:1, about 1300:1, and about 1400:1. Lower ratios of primer to template are preferred to reduce undesirable effects of excess primers in subsequent reactions. Molar ratio of primer to RNA template may be determined as follows: assuming 2% mRNA content in total RNA and an average mRNA size of 2000 bases, each base at 300 g/mol, 5 ng of primer with 5 ng of total RNA is approximately a molar ratio (primer:mRNA) of about 1300:1.

D. DNA Polymerase, Ribonuclease and RNA Polymerase

The amplification methods of the invention employs the following enzymatic activities: DNA polymerase, optionally ribonuclease such as RNase H, and a DNA dependent RNA polymerase. Preferred embodiments of the invention include the use of an RNase H activity, whether present as part of a DNA polymerase activity or as exogenously supplied. Optionally, the methods of the invention include the use of an exonuclease activity (such as but not limited to exonuclease I from *E. coli*, SI nuclease, mung bean exonuclease, or one or more than one single stranded DNA exonuclease in general) to degrade excess primers (not used to prime first strand cDNA synthesis) as needed. Preferred embodiments of the invention include the use of exonuclease I which may be readily inactivated before proceeding on to subsequent reactions. Other preferred embodiments couple the use of exonuclease to degrade excess first primer with the use of an exonuclease deficient polymerase to synthesize the second cDNA strand while protecting the primers used for second strand synthesis.

DNA polymerases for use in the methods and compositions of the present invention are capable of effecting extension of the composite primer according to the methods of the present invention. Accordingly, a preferred polymerase is one that is capable of extending a nucleic acid primer along a nucleic acid template that is comprised at least predominantly of deoxyribonucleotides. The polymerase should be able to displace a nucleic acid strand from the polynucleotide to which the displaced strand is bound, and, generally, the more strand displacement capability the polymerase exhibits (i.e., compared to other polymerases which do not have as much strand displacement capability) is preferable. Preferably, the DNA polymerase has high affinity for binding at the 3'-end of an oligonucleotide hybridized to a nucleic acid strand. Preferably, the DNA polymerase does not possess substantial nicking activity. Preferably, the polymerase has little or no 5'→3' exonuclease activity so as to minimize degradation of primer, termination or primer extension polynucleotides. Generally, this exonuclease activity is dependent on factors such as pH, salt concentration, whether the template is double stranded or single stranded, and so forth, all of which are familiar to one skilled in the art. Mutant DNA polymerases in which the 5'→3' exonuclease activity has been deleted, or in which both 5'→3' and 3'→5 exonuclease activity has been deleted are known in the art and are suitable for the amplification methods described herein. Suitable DNA polymerases for use in the methods and compositions of the present invention may include those disclosed in U.S. Pat. Nos. 5,648,211 and 5744312, which include exo⁻ Vent (New England Biolabs), exo⁻ Deep Vent (New England Biolabs), Bst (BioRad), exo⁻ Pfu (Stratagene), Bca (Panvera), sequencing grade Taq (Promega), and thermostable DNA polymerases from *Thermoanaerobacter thermohydrosulfuricus*. It is preferred that the DNA polymerase displaces primer extension products from the template nucleic acid in at least about 25%, more preferably at least about 50%, even more preferably at least about 75%, and most preferably at least about 90%, of the incidence of contact between the polymerase and the 5' end of the primer extension product. In some embodiments, the use of thermostable DNA polymerases with strand displacement activity is preferred. Such polymerases are known in the art, such as those described in U.S. Pat. No. 5,744,312 (and references cited therein). Preferably, the DNA polymerase has little to no proofreading activity.

While the invention simply requires the use of DNA polymerase activity, the invention is preferably practiced with a combination of polymerase activities wherein the individual polymerases are individually selected from exonuclease deficient Klenow, Taq polymerase, and SEQUENASE™, optionally in the presence of RNase H, in the synthesis of the second strand of the cDNA molecule corresponding to the target polynucleotide. Most preferred is the use of exonuclease deficient Klenow alone or in combination with Taq polymerase in the presence or absence of RNase H. The combination of exonuclease deficient Klenow and Taq polymerase resulted in the unexpected discovery that this combination resulted in improved cDNA synthesis and hence aRNA production over other polymerases. Methods to test and optimize various polymerase activities and conditions, including the identification of activities and conditions which are not suitable for research or commercial applications, for use in the practice of the present invention are known in the art.

Preferred conditions for the use of the exonuclease deficient Klenow and Taq polymerase combination is to permit the Klenow to function at 37° C. followed by an increase in temperature to permit Taq polymerase to function under reduced Klenow activity conditions. In a preferred embodiment of the invention, the two enzymes are added to a mixture of first strand cDNA and random primers when they have been removed (such as, but not limited to, placement in ice or an ice water bath) from heat treatment at about 95° C. The mixture may then be placed at room temperature for about 5 to about 10 minutes followed by an increase to 37° C. for about 10 to about 30 minutes followed by about 72° C. for about 5 to about 15 minutes. In preferred embodiments of the invention, the mixture is maintained at or above room temperature after addition of random primers and DNA polymerase activity and until completion of synthesis of the second cDNA strand.

In alternate embodiments of the invention, the times and temperatures may be adjusted relative to the above conditions, but the time period for second strand cDNA synthesis will preferably not exceed about 3 hours and is preferrably completed in the range of about 1 to about 2 hours. Most preferred is the time period to be less than about one hour or about 30 minutes.

Any reverse transcriptase may be used in the practice of the invention, including, but not limited to, Superscript RTII (optionally RNase H minus), "regular" MMLV-RT (with intrinsic RNaseH activity), AMV RT, or combinations thereof.

The ribonuclease for use in the methods and compositions of the present invention is capable of cleaving ribonucleotides in an RNA/DNA hybrid. Preferably, the ribonuclease cleaves ribonucleotides regardless of the identity and type of nucleotides adjacent to the ribonucleotide to be cleaved. It is preferred that the ribonuclease cleaves independent of sequence identity. Examples of suitable ribonucleases for the methods and compositions of the present invention are well known in the art, including ribonuclease H (RNase H) from *E. coli* or RNaseH associated with retroviral reverse transcriptases.

E. Amplification of Polynucleotides and Anchoring of Amplification Products

The present invention features methods for generating amplification products corresponding to a target polynucleotide wherein the amplification products optionally have one or more anchored known sequences. The starting polynucleotide is a single stranded DNA or RNA which is amplified by the methods of this invention.

In one aspect of the invention, a method for the preparation of a double stranded cDNA from a target RNA polynucleotide is provided. For example, and when a mRNA is the target polynucleotide, the first strand of the cDNA is prepared by the use of a primer, optionally containing an anchor sequence and/or a promoter region, complementary to sequences at or near the 3' end of the mRNA. The primer and target polynucleotide are annealed to form a complex which is then contacted with reverse transcriptase (RT) activity. After primer extension by the RT activity, the mRNA/DNA hybrid duplex may be denatured (by heating or treating with base such as NaOH) to separate the two strands or treated with an RNase H activity (or base such as NaOH) to nick or degrade the mRNA.

Where the mRNA is removed or degraded, the first strand cDNA is contacted with random primers, optionally containing an anchor sequence and/or a promoter region, and allowed to anneal to form complexes which contain random primers hybridized to the first strand cDNA at a plurality of positions. These complexes are then contacted with a DNA dependent DNA polymerase activity to extend the primers and produce the second cDNA strand to form double stranded cDNA. The use of random primers results in a plurality of cDNAs contain all or part of the sequence found in the original target mRNA polynucleotide in individual cDNAs.

As described herein, a variety of DNA polymerase activities may be used, especially activities that are proficient at initiating primer extension reactions and processive in the polymerase activity. A preferred polymerase activity for the practice of the invention is a combination of exonuclease deficient Klenow and Taq polymerase activities as described herein.

It is helpful to note that the method of the invention is distinct from other protocols where the first strand cDNA is contacted with a primer containing a known sequence for annealing to the first strand cDNA. The method is also distinct from coupled reverse transcription/PCR reactions wherein the second strand of the cDNA is synthesized only with a DNA polymerase more active at temperatures above 50° C. than at room temperature ("thermostable polymerase"). The synthesis of the second strand of the cDNA in coupled PCR approach may be viewed as the "first round" of the PCR reaction. The method also differs from PCR in that there is no repetitive thermal cycling of the reaction mixture or the complex between primer and cDNA strand.

Figure 1C:
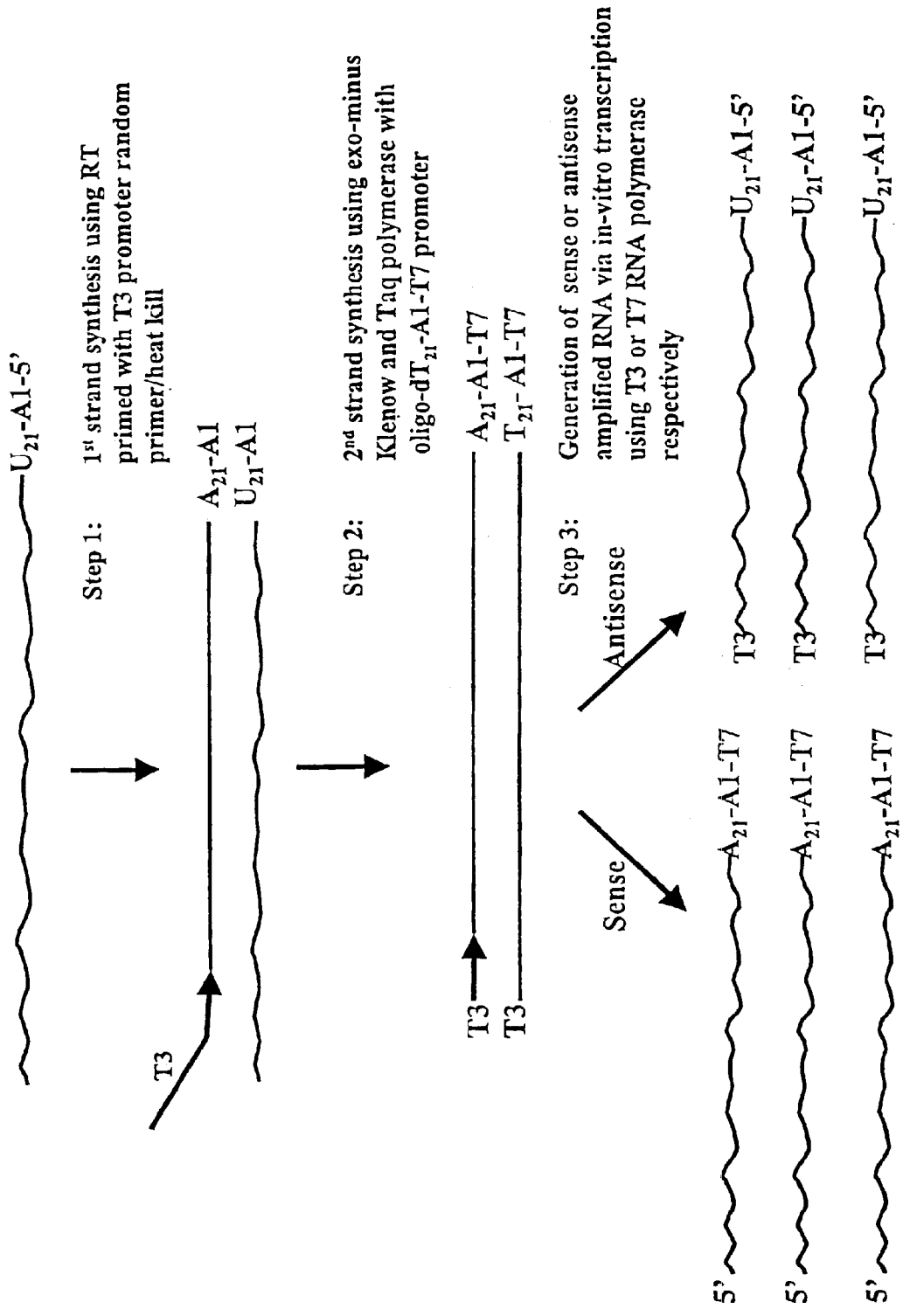
Figure 3A:
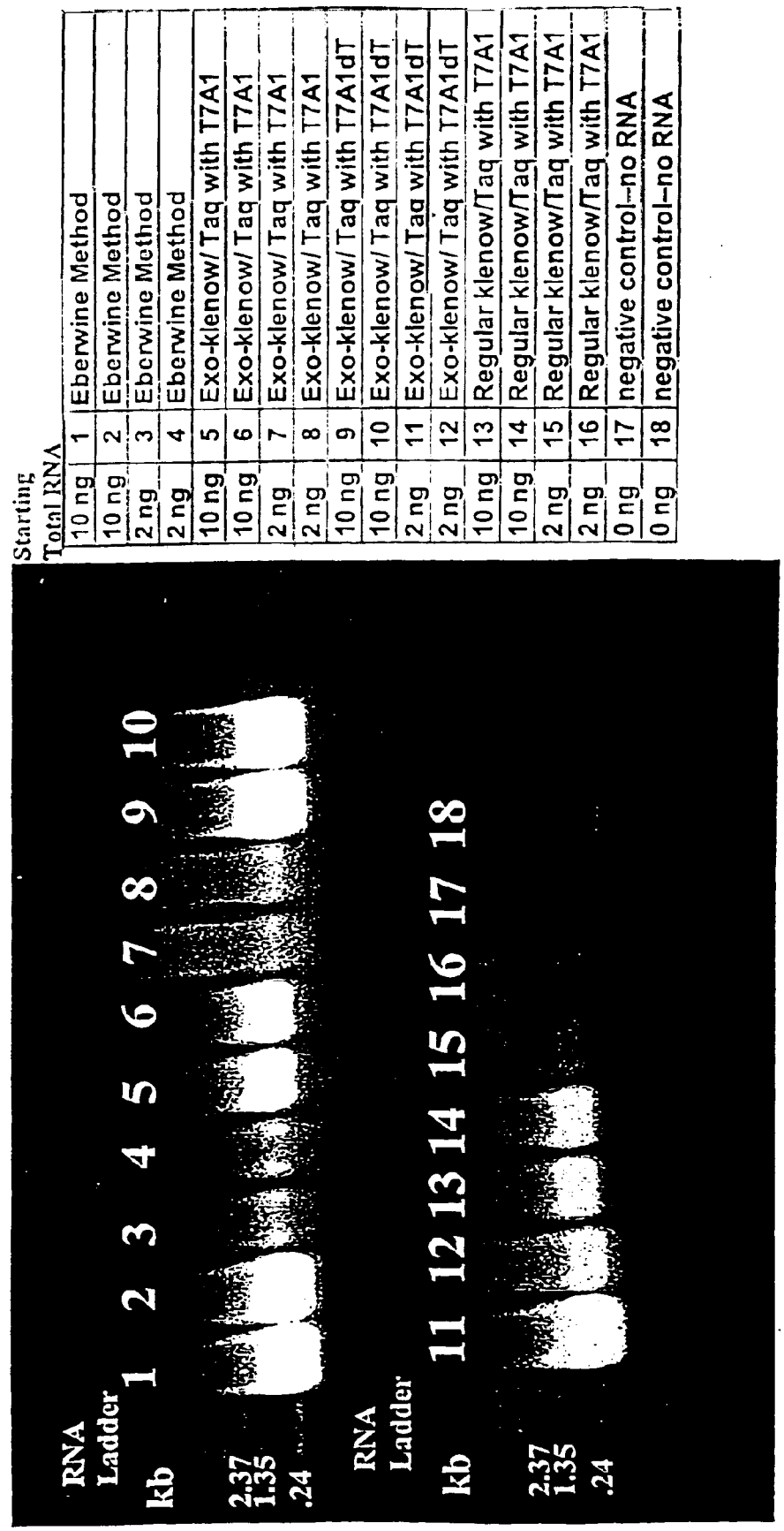

FIG. 1 illustrates an amplification method according to this invention where the template is an eukaryotic mRNA although the use of single or double stranded DNA or non-messenger RNA as template are also encompassed by the method. The method shown in FIG. 1 comprises both "round one" and two possibilities for "round two". "Round one" includes first contacting a (+) strand of a mRNA target with an oligonucleotide comprising poly dT, A1, and T7 promoter sequences. The presence of the A1 anchor sequence is optional and it is not require for the practice of the invention. Since most eukaryotic mRNA molecules are polyadenylated at their 3' end, the oligonucleotide preferably comprises an oligo-dT primer sequence of at least about 8 nucleotides in length and preferably between about 10 and 30 nucleotides in length. A T7 RNA polymerase promoter region is coupled indirectly to the 5' end of the poly-dT primer. Under conditions of the reaction, and as shown in FIG. 1, the poly-dT portion hybridizes to the poly-A stretch at the 3' end of the mRNA target, whereas the promoter sequence does not readily hybridize to the target mRNA.

Where the starting template is not an eukaryotic mRNA (i.e., it does not have a polyA stretch at the 3' end) the first primer sequence may comprise of a degenerate (random) sequence or a specific sequence known to be present at or near the 3' end of the template.

Following extension of the oligonucleotide primer, a (−) first strand cDNA is obtained having a sequence complementary to the mRNA. This cDNA strand comprises an poly dT region and a promoter sequence strand.

The cDNA strand is then separated from the mRNA template by denaturing conditions. These include, but are not limited to, treating the RNA:cDNA duplex with alkali, preferably 0.5 N NaOH, or heating to a temperature (e.g., 95° C.) for a length of time (e.g., 5 minutes) that yields sufficient denaturation. These conditions may also be used to eliminate reverse transcriptase activity prior to further manipulations.

A second oligonucleotide sufficiently complementary to the cDNA strand is then hybridized to the cDNA strand. The second oligonucleotide is exogenously provided and comprises either a random primer or a sequence complementary to a known sequence present in the cDNA strand. A double-stranded DNA is prepared by extending the second oligonucleotide to form a second DNA strand complementary to the cDNA strand in the presence of a DNA-dependent DNA polymerase and appropriate deoxyribonucleotides (dNTPs). A functional double-stranded promoter is thereby formed at an end of the double-stranded DNA operably connected to and upstream of the polynucleotide sequence to be amplified. As shown in FIG. 1, the promoter is operably linked to an end corresponding to the 3' end of the original mRNA template. The promoter may comprise a T3, T7, SP6 or any other suitable RNA polymerase promoter known in the art. For example, and as shown in FIG. 1, a T7 promoter is formed in the process.

The T7 promoter is contacted with the corresponding T7 RNA polymerase enzyme capable of initiating transcription from the promoter, and one or more copies of an amplified RNA (aRNA) is transcribed as the amplification products. The amplified RNAs (aRNAs) comprise in a 5' to 3' order, an poly-U section generated from the poly-dA:dT portion of the double stranded DNA, and a (−) strand sequence complementary to all or part of the mRNA template. Furthermore, most aRNAs can be approximately the same lengths if defined by the hybridization sites of the first and second oligonucleotide primers.

The above may be summarized as a method of amplifying RNA sequences complementary to one or more than one target polynucleotide that is single stranded or made single stranded, comprising a) forming double stranded cDNA templates containing sequences present in said target polynucleotide, wherein said sequences are operably linked to a promoter region, by i) annealing said single stranded target polynucleotide with a first oligonucleotide comprising a primer region operably linked to a promoter region, to form a first complex, ii) synthesizing a first strand cDNA by reverse transcription of said first complex, iii) annealing said first stranded cDNA, after denaturing the mRNA/cDNA hybrid or degrading the RNA from said hybrid, with a plurality of second oligonucleotides comprising a random primer region to form a population of second complexes, and iv) forming double stranded cDNA templates from said population of second complexes with DNA dependent DNA polymerase activity; and b) transcribing said cDNA templates with an RNA polymerase capable of initiating transcription via said promoter region to produce RNA containing sequences complementary to said target polynucleotide. This may be practiced where the target polynucleotide is an mRNA molecule or a plurality of mRNA isolated from a biological source, such as a cell. When mRNA is the target polynucleotide, the first primer region preferably contains a poly dT sequence of about 8 or more nucleotides and the random primer region used to synthesize the second cDNA strand are preferably about six to about nine nucleotides in length. Random primers of more than six, such as seven, eight, nine, ten, eleven, or twelve nucleotides, are preferably used. Preferably, the second cDNA strand is synthesized by use of exonuclease deficient Klenow and Taq polymerase activities.

Of course in any embodiment of the invention any of the nucleic acids (DNA or RNA) may be labeled during the synthesis of the polynucleotide chain.

In an optional embodiment of the invention, the synthesis of the first and/or second cDNA strand is conducted in the presence of a repetitive polynucleotide such as, but not limited to, polymers of deoxyribo- or ribo-nucleotides of adenosine, cytosine, thymidine, guanine, or inosine. Particularly preferred is the use of poly adenosine (poly A), poly dA, and poly inosine (poly I). The inclusion of such polymers may be especially advantageous in situations where the amount of the target polynucleotide, especially target mRNA, is very low, such as in the picogram range. When higher amounts of target are higher, such as in the nanogram range, there is less added benefit to the inclusion of such polymers.

In "round two" of FIG. 1, the aRNA of "round one" is used as the template to prepare additional double stranded DNAs to amplify more aRNA. This is exemplified by the use of a primer to generate a first strand DNA which is complementary to all or part of the aRNA template, followed by generation of the second strand DNA by use of the T7 promoter containing oligonucleotide from "round one". The resultant double stranded DNA may be used to transcribe aRNAs containing all or part of the sequences of the aRNA template. The transcribed aRNAs would contain all of the sequences of the aRNA template if the primer used to generate the first strand DNA was complementary to the 3' end of the aRNA template. The transcribed aRNAs would contain part of the sequences of the aRNA template if the primer used to generate the first strand DNA was complementary to an internal portion of the aRNA template.

The above may be summarized as increasing the amplification of RNA sequences complementary to a target polynucleotide by preparing additional double stranded DNA templates, comprising all or part of the sequence of the aRNA, and initiating transcription from the additional templates, by annealing said aRNA to a third oligonucleotide comprising a primer region to form a third complex, synthesizing the first strand of said additional double stranded DNA templates by reverse transcription of said third complex, annealing said first strand of additional DNA templates, after denaturing the aRNA/DNA hybrids or degrading the aRNA from said hybrids, with said first oligonucleotide comprising an operably linked promoter region to form a fourth complex, forming additional double stranded DNA templates from said fourth complex with DNA dependent DNA polymerase activity, and transcribing said double stranded DNA templates with an RNA polymerase capable of initiating transcription via said promoter region to produce additional amplified RNA (aRNA) containing sequences complementary to said target polynucleotide. The random primer region of the third oligonucleotide is preferably about six to about nine nucleotides in length and a combination of exonuclease deficient Klenow and Taq polymerase activities is preferably used to synthesize the double stranded DNA templates from the fourth complex. Alternatively, the third oligonucleotide may comprise a known primer sequence, optionally complementary to the 3' end of aRNA. In "round two modified" as shown in FIG. 1, the aRNA of "round one" is used to prepare additional double stranded DNAs containing promoters at both ends. This is exemplified by the use of a T3 promoter containing primer to generate a first strand DNA which is complementary to all or part of the aRNA template, followed by generation of the second strand DNA by use of the T7 promoter containing oligonucleotide from "round one". Optionally, this oligonucleotide may be modified to exclude the promoter introduced in "round one" so that the method may be adapted to exclude replication of the promoter region introduced in "round one". The resultant double stranded DNA may be used to transcribe aRNAs containing all or part of the sequences of the aRNA template (by using a T7 RNA polymerase) or to transcribe a sequence complementary to all or part of the aRNA template (by using a T3 RNA polymerase). The transcribed aRNAs would contain all of the sequences of the aRNA template if the primer used to generate the first strand DNA was complementary to the 3' end of the aRNA template. The transcribed aRNAs would contain part of the sequences of the aRNA template if the primer used to generate the first strand DNA was complementary to an internal portion of the aRNA template.

The above may be summarized as a method of amplifying RNA sequences present in one or more than one target polynucleotide that is single stranded or made single stranded by modifying "round two" by i) annealing said aRNA with a third oligonucleotide comprising a primer region operably linked to a promoter region to form a third complex, ii) synthesizing the first strand of said additional DNA template by reverse transcription of said third complex, iii) annealing said first strand of additional DNA template, after denaturing the aRNA/DNA hybrid or degrading the aRNA from said hybrid, with said first oligonucleotide to form a population of fourth complexes, and iv) forming additional double stranded DNA templates from said population of fourth complexes with DNA dependent DNA polymerase activity; and then transcribing said additional DNA templates with an RNA polymerase capable of initiating transcription via the promoter region of said first oligonucleotide to produce amplified RNA (aRNA) containing sequences complementary to said target polynucleotide or via the promoter region of said third oligonucleotide to produce aRNA containing sequences present in said target polynucleotide. The third oligonucleotide may again comprise a random primer region, preferably from at least about six random nucleotides to at least about nine random nucleotides, or a known primer sequence, optionally complementary to the 3' end of said aRNA. The promoter region of the third oligonucleotide preferably comprises a T3 promoter region.

In all of the above, the promoter region of the first oligonucleotide preferably comprises a T7 promoter region.

F. Additional Rounds of Amplification

Where the total levels of starting RNA target polynucleotide is limiting (e.g., <20 ng of total RNA or <~400 pg of mRNA in the form of poly (A) RNA), the second and further rounds of amplification of the aRNA may be performed according to methods of the present invention. Such additional rounds may of course be performed more than once, such as, but not limited to, twice, three times, or four times.

The amplification, which will typically be at least about 20–40, typically to 50 to 100 or 250-fold, or 500 to 1000-fold, or 500–2000 fold or more per round of amplification, can be achieved from nanogram quantities or less of total RNA (and thus picograms of starting material of poly(A) RNA), and is economical and simple to perform under standard molecular biology laboratory conditions. It is also easily adaptable into kit form.

In an optional embodiment of the invention, the synthesis of one or both cDNA strands is conducted in the presence of a repetitive polynucleotide such as, but not limited to, polymers of deoxyribo- or ribo-nucleotides of adenosine, cytosine, thymidine, guanine, or inosine. Particularly preferred is the use of poly adenosine (poly A), poly dA, and poly inosine (poly I). The inclusion of such polymers may be especially advantageous in situations where the amount of the target polynucleotide, especially target mRNA, is very low, such as in the picogram range. When higher amounts of target are higher, such as in the nanogram range, there is less added benefit to the inclusion of such polymers.

Use of poly I in the purification of total RNA has been evaluated by Winslow et al. (Nucl. Acids Res. 19(12):3251–3253 1991).

G. Uses: Detection of Polynucleotide Expression and Related Diagnostic Methods

In specific non-limiting embodiments, the present invention provides methods useful for detecting cancer cells, facilitating diagnosis of cancer and the severity of a cancer (e.g., tumor grade, tumor burden, and the like) in a subject, facilitating a determination of the prognosis of a subject, and assessing the responsiveness of the subject to therapy (e.g., by providing a measure of therapeutic effect through, for example, assessing tumor burden during or following a chemotherapeutic regimen). Detection can be based on detection of a polynucleotide that is differentially expressed in a cell, and/or detection of a polypeptide encoded by a polynucleotide that is differentially expressed in a cell. The detection methods of the invention can be conducted in vitro or in vivo, on isolated cells, or in whole tissues or a bodily fluid (e.g., blood, plasma, serum, urine, and the like).

The aRNA of mRNAs from live or fixed (from tissue sections via laser capture microdissection or other means of dissection), single or multiple cells can be amplified sufficiently to generate the following: labeled probes for hybridization experiments (e.g., DNA microarrays or macroarrays) thus generating gene expression profiles of various cell types or individual cells (in a manner analogous to that disclosed by Serafini et al., U.S. Pat. No. 6,110,711); cDNA libraries that contain mRNAs from selected cells and subsequently used to generate normalized libraries or various subtractive hybridization methodologies; cDNA that then is used for RT-PCR or quantitative RT-PCR (to subsequently quantitate individual mRNAs); cDNA for subsequent use for various methods that yield differentially expressed genes (i.e., differential display and representational difference analysis (RDA)); and amplified RNA that can be used in various subtraction methodologies, such as subtractive hybridization. The amplification of mRNAs from a single cell is a preferred embodiment of the invention and offers advantages in eliminating the possibility of amplifying heterologous mRNA due to the use of two or more cells.

As noted above, the methods of the present invention may be used to detect expression of a particular gene sequence (including, but not limited to, sequences that differ due to genetic polymorphism) on a cell or population of cells by determining the presence or absence of RNA transcribed from the particular gene sequence in the amplified RNA population. The level of expression of the particular gene may also be determined relative to other RNAs amplified within the overall population of amplified RNAs. The level of expression between different tissues or cell types (or different physiological states of the same tissue or cell type) may also be compared by preparing amplified RNAs from the different tissues or cell types (or the same tissue or cell type under different physiological states, such as, but not limited to, cancer and non-cancer cells) and comparing the species of amplified RNAs produced from the different sources. Different physiological states of the invention include, but are not limited to, different drug (or other active agent) induced states, different behavioral states, different developmental states, different states of stimulation, different states of activation or inhibition, or different states of arousal.

The present methods may also be used to produce amplified RNAs that are used as subtractive hybridization probes or used as the templates for members of a cDNA library (after a second round of amplification and without in vitro transcription, for example). The techniques for subtractive hybridization are known in the art, and the use of the present methods provide an advantageous means of producing RNAs for use in subtraction. Similarly, the techniques for preparing a cDNA library are known in the art and the present methods provide an advantageous means of producing the member sequences of a library.

H. Labeling and Detection of Amplified Molecules

Detecting labeled target polynucleotides can be conducted by standard methods used to detect the labeled sequences. For example, fluorescent labels or radiolabels can be detected directly such as incorporating fluorescent nucleotide dyes into cDNA generation using amplified RNA as template. Other labeling techniques may require that a label such as biotin or digoxigenin be incorporated into the DNA or RNA (during amplification or within cDNA generated from amplified RNA) and detected by an antibody or other binding molecule (e.g. streptavidin) that is either labeled or which can bind a labeled molecule itself. For example, a labeled molecule can be an anti-streptavidin antibody or anti-digoxigenin antibody conjugated to either a fluorescent molecule (e.g. fluorescein isothiocyanate, Texas red and rhodamine), or an enzymatically active molecule. Whatever the label on the newly synthesized molecules, and whether the label is directly in the DNA or conjugated to a molecule that binds the DNA (or binds a molecule that binds the DNA), the labels (e.g. fluorescent, enzymatic, chemiluminescent, or colorimetric) can be detected by a laser scanner or a CCD camera, or X-ray film, depending on the label, or other appropriate means for detecting a particular label.

The amplified target polynucleotide can be detected by using labeled nucleotides (e.g. dNTP-fluorescent label for direct labeling; and dNTP-biotin or dNTP-digoxigenin for indirect labeling) incorporated during amplification or by incorporating it during cDNA synthesis when using amplified RNA as template. For indirectly labeled DNA, the detection is carried out by fluorescence or other enzyme conjugated streptavidin or anti-digoxigenin antibodies. The method employs detection of the polynucleotides by detecting incorporated label in the newly synthesized complements to the polynucleotide targets. For this purpose, any label that can be incorporated into DNA as it is synthesized can be used, e.g. fluoro-dNTP, biotin-dNTP, or digoxigenin-dNTP, as described above and are known in the art. In a differential expression system, amplification products derived from different biological sources can be detected by differentially (e.g., red dye and green dye) labeling the amplified target polynucleotides based on their origins.

In a preferred embodiment, amplified RNA is used as template for incorporating fluorescent nucleotides during the subsequent probe generation via cDNA synthesis.

For detection, light detectable means are preferred, although other methods of detection may be employed, such as radioactivity, atomic spectrun, and the like. For light detectable means, one may use fluorescence, phosphorescence, absorption, chemiluminescence, or the like. The most convenient will be fluorescence, which may take many forms. One may use individual fluorescers or pairs of fluorescers, particularly where one wishes to have a plurality of emission wavelengths with large Stokes shifts (at least 20 nm). Illustrative fluorescers include fluorescein, rhodamine, Texas red, cyanine dyes, phycoerythrins, thiazole orange and blue, etc.

Depending on the particular intended use of the aRNA, the aRNA may be labeled. One way of labeling which may find use in the subject invention is isotopic labeling, in which one or more of the nucleotides is labeled with a radioactive label, such as $^{32}S$, $^{32}P$, $^{3}H$, or the like. Another means of labeling is fluorescent labeling in which a fluorescently tagged nucleotide, e.g. CTP, is incorporated into the aRNA product during transcription. Fluorescent moieties which may be used to tag nucleotides for producing labeled antisense RNA include: fluorescein, the cyanine dyes, such as Cy3, Cy5, Alexa 542, Bodipy 630/650, and the like.

I. Characterization of Nucleic Acids

The amplification products obtained by the methods of the invention are particularly amenable to further characterization, in part because the products are single stranded. The amplified products, either DNA or RNA, can analyzed using probe hybridization techniques known in the art, such as Southern and Northern blotting on a solid support such as, but not limited to, nitrocellulose. The amplified products can also be analyzed by contacting them with microarrays comprising oligonucleotide probes or cDNAs. The identity of the probes provides characterization of the sequence identity of the amplified products, and thus by extrapolation the identity of the template nucleic acid present in a sample suspected of containing said template nucleic acid. The above hybridization based techniques may also be used to detect expression from a single gene sequence.

J. Kits

Also provided are kits for use in the subject invention, where such kits may comprise containers, each with one or more of the various reagents (typically in concentrated form) utilized in the methods, including, for example, buffers, the appropriate nucleotide triphosphates (e.g. dATP, dCTP, dGTP, dTTP, dUTP, ATP, CTP, GTP and UTP), reverse transcriptase, DNA polymerase, RNA polymerase, and one or more sequence-specific primers, degenerate primers, random primers, poly-dT primers and corresponding promoter-primers and tagged-primers of the present invention. A label or indicator describing, or a set of instructions for use of, kit components in an mRNA amplification method of the present invention, will also be typically included, where the instructions may be associated with a package insert and/or the packaging of the kit or the components thereof.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all and only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

Example 1

Transcription from T7 RNA Polymerase Promoter

In one general embodiment of the present invention, cDNA strands are synthesized from a collection of mRNAs using an oligonucleotide primer complex. If the target mRNA is the entire mRNA population, then the primer can be a polythymidylate region (e.g., about 5 to 25, preferably about 18–21 T residues), which will bind with the poly(A) tail present on the 3 terminus of each mRNA. Alternatively, if only a preselected mRNA is to be amplified, then the primer will be substantially complementary to a section of the chosen mRNA, typically at the 3' terminus. The promoter region is located upstream of the primer at its 5' terminus in an orientation permitting transcription with respect to the mRNA population utilized. When the second cDNA strand is synthesized, the promoter sequence will be in correct orientation in that strand to initiate RNA synthesis using that second cDNA strand as a template. Preferably, the promoter region is derived from a prokaryote, and more preferably from the group consisting of SP6, T3 and T7 phages (Chamberlin and Ryan, in The Enzymes, ed. P. Boyer (Academic Press, New York) pp. 87–108 (1982), which is incorporated herein by reference). A preferred promoter region is one that contains an arbitrary sequence (here for example, part of the M13 forward priming site) 5' to the consensus T7 promoter sequence." (5' AAA CGA CGG CCA GTG AAT TGT AAT ACG ACT CAC TAT AGG GAG A 3', SEQ ID NO:1).

Once the oligonucleotide primer hybridizes to the mRNA, a first DNA strand is synthesized. This first strand of cDNA is preferably produced through the process of reverse transcription, wherein DNA is made from RNA, utilizing reverse transcriptase following standard techniques. This enzyme, (e.g., MMLV reverse transcriptase or AMV reverse transcriptase), adds deoxyribonucleotides to the 3' terminus of the primer (Varmus, Science 240:1427–1435 (1988)).

To complete second strand synthesis, random nonamers (9-mers) are added to the RNA/cDNA heteroduplex that has been previously denatured, and with the use of a DNA polymerase (preferably Klenow plus Taq or exo-Klenow plus Taq) and dNTPs, the second strand is synthesized. The second strand is generated as deoxyribonucleotides are added to the 3' terminus of the growing strand. As the growing strand reaches the 5' terminus of the first strand DNA, the complementary promoter region of the first strand will be copied into the double stranded promoter sequence in the desired orientation.

Once double stranded cDNA is synthesized then T7 RNA polymerase is used to generate a plurality of aRNAs via transcription from the cDNA template. Preferred transcription conditions employ a class III T7 promoter sequence and a T7 RNA polymerase under the following reaction conditions: 40 mM Tris pH 7.9, 6 or 10 mM $MgCl_2$, 2 mM Spermidine, 10 mM DTT, 2 mM NTP (Pharmacia), 40 units RNAsin (Promega), 300–1000 units T7 RNA Polymerase (Promega). The enzyme is stored in 20 mM HEPES pH 7.5, 100 mM NaCl, 1 mM EDTA, 1 mM DTT and 50% Glycerol at a protein concentration of 2.5 mg/ml and an activity of 300–350 units/$\mu$l. In exemplary demonstrations, 1–3 $\mu$L of this polymerase was used in 50 $\mu$L reactions (commercially available transcription kits may be used in this step). Starting concentrations of template can vary from sub-picogram quantities (single cell level) to 1 $\mu$g or more of linear DNA.

The DNA is transcribed into anti-sense RNA (aRNA) by introducing an RNA polymerase capable of binding to the promoter region. Amplification occurs because the polymerase repeatedly recycles on the template (i.e., reinitiates transcription from the promoter region). This particular technique enables replicating a broad range of cDNAs without prior cloning into vectors. Recycling of the polymerase on the same template avoids propagation of errors.

Example 2

Source of Cell Samples and Isolation of Expressed Polynucleotides

Normalized cDNA library is prepared from one patient tumor tissue and cloned polynucleotides for spotting on microarrays are isolated from the library. Normal and tumor tissues from other patients are processed to generate amplified aRNA, which are, in turn, assessed for expression in microarrays. The objective of normalization is to generate a cDNA library in which all transcripts expressed in a particular cell type or tissue are equally represented (Weissman SM Mol Biol. Med. 4(3),133–143 (1987); Patanjali, et al. Proc. Natl. Acad. Sci. USA 88 (1991)), and therefore isolation of as few as 30,000 recombinant clones in an optimally normalized library may represent the entire gene expression repertoire of a cell, estimated to number 10,000 per cell.

Cells (~100–500 cells) are harvested directly from frozen sections of tissue by laser capture microdissection (LCM, Arcturus Engineering Inc., Mountain View, Calif.), carried out according to methods well known in the art (see, Simone et al. Am J Pathol. 156(2):445–52 (2000)), to provide substantially homogenous cell samples. Total RNA is extracted from LCM-harvested cells using any known protocol (such as, but not limited to, commercially available kits including Picopure™ from Arcturus Engineering Inc., Mountain View, Calif.). About 2–10 ng of total RNA (approximate yield from 100–500 cells) is reverse transcribed into cDNA and subsequently amplified via two rounds as detailed in this invention (see example 1) using the modified second round. In this case (i.e., using the modified second round), the resultant aRNA generated via T7 RNA polymerase after two rounds of amplification has the following sequence 5' to 3': anchor 1 sequence, $U_{21}$, polynucleotide sequence of a given mRNA, followed by T3 promoter sequence. The resultant aRNA from two rounds of amplification is converted into double stranded cDNA using a primer for first strand synthesis that contains the T3 sequence. Second strand synthesis is initiated via a primer containing, from 5' to 3', the T7 promoter sequence, anchor 1 followed by 21 dT's. The subsequent cDNA products are sizeselected by agarose gel electrophoresis using standard procedures to remove small sized cDNA (<100 bp) (Sambrook, J. T., et al. Molecular Cloning: A Laboratory Manual, 2d ed., Cold Spring Harbor Laboratory Press, NY). The cDNA is extracted by any known method including, but not limited to commercially available kits, followed by normalization of the cDNA using kinetics of hybridization principles: 1.0 µg of cDNA is denatured by heat at 100° C. for 10 minutes, and then incubated at 42° C for at least 12 hours in the presence of 120 mM NaCl, 10 mM Tris.HCl (pH=8.0), 5 mM EDTA.Na+ and 50% formamide. Single-stranded cDNA ("normalized" cDNA) was purified by hydroxyapatite chromatography (#130–0520, BioRad, Hercules, Calif.) following the manufacturer's recommended procedures, amplified into double stranded cDNA via PCR using two oligonucleotide primers containing T3 and T7 promoter sequences respectively, and subsequently cloned into plasmid vectors using standard procedures (Sambrook, J. T., et al. Molecular Cloning: A Laboratory Manual, 2d ed., Cold Spring Harbor Laboratory Press, NY). Supercompetent cells (XL-2 Blue Ultracompetent Cells, Stratagene, California) are transfected with the normalized cDNA libraries, plated on solid media and grown overnight at 37° C.

Example 3

Differential Expression Assay cDNA probes are prepared from RNA amplified via the present invention from total RNA that has been extracted from normal and cancerous cells that are contained within a biopsy/surgical resection procured via laser capture microdissection (LCM, Arcturus Engineering Inc., Mountain View, Calif.). Fluorescently labeled cDNAs prepared from the tumor sample are compared to fluorescently labeled cDNAs prepared from normal cell sample. For example, the cDNA probes from normal cells are labeled with Cy3 fluorescent dye (green) and cDNA probes prepared from the tumor cells are labeled with Cy5 fluorescent dye (red).

The differential expression assay is performed by probing equal amounts of probes from tumor cells and normal cells of the same patient. The fluorescently labeled probes are hybridized to the array under conditions of high stringency (overnight at 42° C. in 50% formamide, 5×SSC, and 0.2% SDS). After hybridization, the array is washed at 55° C. three times as follows: 1) first wash in 1×SSC/0.2% SDS; 2) second wash in 0.1×SSC/0.2% SDS; and 3) third wash in 0.1×SSC.

The arrays are then scanned for green and red fluorescence using a laserscanner/detector. The images are processed using BioDiscovery Autogene software, and the data from each scan set normalized. The experiment is repeated, this time labeling the two probes with the opposite color in order to perform the assay in both "color directions." Each experiment is sometimes repeated with two more slides (one in each color direction). The data from each scan is normalized, and the level fluorescence for each sequence on the array expressed as a ratio of the geometric mean of 8 replicate spots/genes from the four arrays or 4 replicate spots/gene from 2 arrays or some other permutation.

Example 4

Detailed Embodiment with Optional Second Round

Synthesis of the First cDNA Strand

A RNA sample (of about 5 ng RNA) containing one or more target mRNAs of interest is prepared in a small (e.g. about 5 to about 20 µL) volume of water in a small tube. A first oligonucleotide primer (from about 5 ng to about 25 or about 50 or about 75 ng) comprising a poly dT region and one strand of a RNA polymerase promoter region coupled to the 5' end of the poly dT region (such that if made duplex with the complementary strand, the promoter would initiate transcription that proceeds in the 5' to 3' direction of the poly dT region) is added to the RNA sample. The sample is briefly heated (e.g. from about 65–99° C.) for a short period (e.g. from about 5 to about 15 minutes) followed by chilling on ice or at about 4° C. until ready for use.

The sample is then adjusted to conditions for reverse transcription, and reverse transcriptase activity, optionally including endogenous RNase H activity and RNase inhibitors, is added while maintaining the mixture in a small volume. The reaction mixture is then incubated (e.g. from about 37 to about 45° C.) for about 1 hour followed by heating (e.g. from about 65–99° C.) for a short period (e.g. from about 5 to about 15 minutes). The synthesis of the first strands of cDNA corresponding to target mRNAs is completed at this point, and reverse transcriptase activity is inactivated by heating. In preferred embodiments where exonuclease is used to degrade primers after reverse transcription, the heating is preferably from about 65–70° C. to prevent denaturation of duplex nucleic acids before the exonuclease treatment. The mixture is then chilled on ice or at about 4° C. for a short period.

In preferred embodiments where unused primers are degraded, a small volume containing exonuclease I or other single stranded DNA exonuclease activity (for example, but not limited to, about 20–60 units of E. coli exonuclease I activity) is added to the reaction mixture followed by incubation at about 37° C. for about 5 to about 30 minutes. The reaction mixture is then heated at high temperature (e.g. from about 95–99° C.) for a short period (e.g. from about 5 to about 15 minutes) to inactivate enzymatic activities and denature duplex nucleic acids. The mixture is then chilled on ice or at about 4° C. until ready for use. It should be noted that any duplex nucleic acids that formed as a result of reverse transcriptase activity has been rendered completely denatured by high temperature heating.

Synthesis of the Second cDNA Strand

Random primers are added to the above chilled mixture followed by heating at high temperature (e.g. from about 95–99° C.) for a short period (e.g. from about 2 to about 10 minutes) followed by cooling on ice or at about 4° C. for a short period (e.g. from about 2 to about 10 minutes). The mixture is then adjusted to conditions for DNA dependent DNA synthesis, and DNA polymerase activity, preferably a combination of Taq polymerase and exo⁻ Klenow is added. DNA synthesis may then proceed under multiple incubation conditions (e.g. about 25° C. or room temperature for about 10 minutes followed by about 37° C. for about 30 minutes followed optionally by about 70 or 72° C. for about 15 minutes). The reaction is then cooled on ice or at about 4° C. until ready to proceed. The synthesis of double stranded cDNA is complete at this point.

The cDNA may be optionally purified by any means known in the art. In this embodiment of the invention, the cDNA is purified by use of a spin column. Briefly, the reaction mixture is combined with a volume of column buffer and added to a prepped column. The column is centrifuged briefly and the flow-through discarded. A wash buffer is added and the column centrifuged again with the flow through discarded again. Finally, a volume of elution buffer is added and the column spun once more with collection and retention of the eluate as containing the cDNA. The eluate may be further concentrated to place the cDNA into a smaller volume.

RNA Amplification/in vitro Transcription

The cDNA from the above reaction (or a sample thereof) is made to be in a solution under conditions suitable for in vitro transcription, and an RNA polymerase capable of initiating transcription from the promoter region present in the first oligonucleotide primer (described above) is added. The reaction is then incubated (e.g. from about 37 to about 45° C.) for about 2 to about 4 or about 6 hours.

Optionally, RNase free DNase may be added to degrade the cDNA template prior to further use. The resultant (transcribed) amplified RNA may be optionally purified, such as by the use of a spin column analogous to that described above, and then concentrated. The resultant amplified RNA may be used to prepare labeled cDNA or used optionally as the starting material for a second round of amplification.

Second Round

The second round begins with the addition of random primers followed by heating (e.g. from about 70 to about 80° C.) for a short period (e.g. from about 5 to about 15 minutes) followed by cooling on ice or at about 4° C. for a short period (e.g. from about 1 to about 10 minutes). The mixture is then adjusted to conditions for reverse transcription, and reverse transcriptase activity, optionally including endogenous RNase H activity and RNase inhibitors, is added. The reaction mixture is then incubated (e.g. from about 25 to about 37° C., optionally in two steps) for about 10 to about 90 minutes followed by heating (e.g. from about 65–99° C.) for a short period (e.g. from about 5 to about 15 minutes). The synthesis of the first strands of cDNA corresponding to the amplified RNAs is completed at this point, and reverse transcriptase activity may be inactivated by the heating step. The mixture is then chilled on ice or at about 4° C. for a short or indefinite period.

The first oligonucleotide primer (described above) is then added to the mixture followed by heating at a high temperature (e.g. about 95–99° C.) for a short period (e.g. from about 2 to about 15 minutes). The mixture is again chilled on ice or at about 4° C. for a short period followed by adjustment of the mixture to be suitable for DNA dependent DNA synthesis. DNA polymerase activity, preferably a combination of Taq polymerase and exo⁻ Klenow is added, and DNA synthesis allowed to proceed under multiple incubation conditions (e.g. about 37° C. for about 30 minutes followed by about 70° C. for about 15 minutes). The reaction is then cooled on ice or at about 4° C. until ready to proceed. The synthesis of double stranded DNA is complete at this point and the DNA may be purified as described above.

The purified DNA may then be used for RNA amplification (in vitro transcription), and subsequent RNA purification and use, as described above.

All references cited herein, including patents, patent applications, and publications, are hereby incorporated by reference in their entireties, whether previously specifically incorporated or not, for all purposes. Citation of any reference herein is not intended as an admission that any of the foregoing is pertinent prior art, nor does it constitute any admission as to the contents or date of these documents.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method of amplifying RNA sequences complementary to one or more than one target polynucleotide that is single stranded or made single stranded, comprising
   a) forming double stranded cDNA templates containing sequences present in said target polynucleotide, wherein said sequences are operably linked to a promoter region, by
      i) annealing said one or more than one single stranded target polynucleotide with a first oligonucleotide comprising a primer operably linked to a promoter region to form a first complex,
      ii) synthesizing one or more than one first strand cDNA by reverse transcription of said first complex,
      iii) degrading first oligonucleotides not used in i) or ii) above with exonuclease activity,
      iv) annealing said one or more than one first strand cDNA, after denaturing the hybrid(s) of single stranded target polynucleotide and cDNA or degrading the single stranded target polynucleotide from said hybrid(s), with a plurality of second oligonucleotides comprising a random primer region to form a population of second complexes, and
      v) forming one or more than one double stranded cDNA templates from said population of second complexes with DNA polymerase activity; and
   b) transcribing said cDNA templates with an RNA polymerase capable of initiating transcription via said promoter region to produce amplified RNA (aRNA) containing sequences complementary to said one or more than one target polynucleotide.

2. The method of claim 1 wherein said target polynucleotide is mRNA.

3. The method of claim 1 wherein said more than one target polynucleotide are a cellular mRNA preparation.

4. The method of claim 1 wherein said first oligonucleotide comprises a primer containing an oligo or poly dT sequence.

5. The method of claim 4 wherein said oligo or poly dT sequence is at least about eight dT in length.

6. A method of amplifying RNA sequences complementary to one or more than one target polynucleotide that is single stranded or made smile stranded, comprising
   a) forming double stranded cDNA templates containing sequences present in said target polynucleotide, wherein said sequences are operably linked to a promoter region, by
      i) annealing said one or more than one single stranded target polynucleotide with a first oligonucleotide comprising a primer operably linked to a promoter region to form a first complex,
      ii) synthesizing one or more than one first strand cDNA by reverse transcription of said first complex,
      iii) degrading first oligonucleotides not used in i) or ii) above with exonuclease activity,
      iv) annealing said one or more than one first strand cDNA, after denaturing the hybrid(s) of single stranded target polynucleotide and cDNA or degrading the single stranded target polynucleotide from said hybrid(s), with a plurality of second oligonucleotides comprising a random primer region comprising at least about six random nucleotides to form a population of second complexes, and
      v) forming one or more than one double stranded cDNA templates from said population of second complexes with DNA polymerase activity; and
   b) transcribing said cDNA templates with an RNA polymerase capable of initiating transcription via said promoter region to produce amplified RNA (aRNA) containing sequences complementary to said one or more than one target polynucleotide.

7. The method of claim 6 wherein said random primer region comprises at least about nine random nucleotides.

8. The method of claim 1 wherein said DNA polymerase activity is DNA dependent.

9. The method of claim 8 wherein said DNA dependent polymerase activity is selected from exonuclease deficient Klenow, Taq polymerase activities, and combinations of exonuclease deficient Klenow and/or Taq polymerase activities.

10. The method of any of claims 1–8 wherein the amplification of RNA sequences complementary to one or more than one target polynucleotide is increased by preparing additional double stranded DNA templates, comprising all or part of the sequence of the aRNA, and initiating transcription from the additional templates, said method comprising
    annealing said aRNA to a third oligonucleotide comprising a primer region to form a third complex,
    synthesizing the first strand of said additional double stranded DNA templates by reverse transcription of said third complex to produce an aRNA/DNA hybrid,
    annealing said first strand of additional DNA templates, after denaturing the aRNA/DNA hybrids or degrading the aRNA from said hybrids, with said first oligonucleotide comprising an operably linked promoter region to form a fourth complex,
    forming additional double stranded DNA templates from said fourth complex with DNA dependent DNA polymerase activity, and
    transcribing said double stranded DNA templates with an RNA polymerase capable of initiating transcription via said promoter region to produce additional amplified RNA (aRNA) containing sequences complementary to said target polynucleotide,
    wherein the above annealing, synthesizing, annealing, forming and/or transcribing acts of the method are optionally repeated to further amplify said RNA sequences complementary to one or more than one target polynucleotide.

11. The method of claim 10 wherein said third oligonucleotide comprises a random primer region.

12. The method of claim 11 wherein said random primer region comprises at least about six random nucleotides.

13. The method of claim 12 wherein said random primer region comprises at least about nine random nucleotides.

14. The method of claim 10 wherein said DNA dependent DNA polymerase activity comprises exonuclease deficient Klenow and Taq polymerase activities.

15. The method of claim 10 wherein said third oligonucleotide comprises a known primer sequence.

16. The method of claim 15 wherein said known primer sequence is complementary to the 3' region of said aRNA.

17. A method of amplifying RNA sequences complementary to, or present in, one or more than one target polynucleotide that is single stranded or made single stranded, comprising
    a) forming double stranded cDNA templates containing sequences present in said target polynucleotide, wherein said sequences are operably linked to a promoter region, by
      i) annealing said one or more than one single stranded target polynucleotide with a first oligonucleotide comprising a primer operably linked to a promoter region to form a first complex, ii) synthesizing one or more than one first strand cDNA by reverse transcription of said first complex, iii) degrading first oligonucleotides not used in i) or ii) above with exonuclease activity, iv) annealing said one or more than one first stranded cDNA, after denaturing the hybrid(s) of single stranded target polynucleotide and cDNA or degrading the single stranded target polynucleotide from said hybrid(s), with a plurality of second oligonucleotides comprising a random primer region to form a population of second complexes, and v) forming one or more than one double stranded cDNA templates from said population of second complexes with DNA dependent DNA polymerase activity, and b) transcribing said cDNA templates with an RNA polymerase capable of initiating transcription via said promoter region to produce amplified RNA (aRNA) containing sequences complementary to said one or more than one target polynucleotide c) forming additional double stranded DNA templates from said aRNA by i) annealing said aRNA with a third oligonucleotide comprising a primer region operably linked to a promoter region to form a third complex, ii) synthesizing the first strand of said additional DNA template by reverse transcription of said third complex to produce an aRNA/DNA hybrid, iii) annealing said first strand of additional DNA template, after denaturing the aRNA/DNA hybrid or degrading the aRNA from said hybrid, with said first oligonucleotide to form a population of fourth complexes, and iv) forming additional double stranded DNA templates from said population of fourth complexes with DNA dependent DNA polymerase activity; and d) transcribing said additional DNA templates with an RNA polymerase capable of initiating transcription via the promoter region of said first oligonucleotide to produce amplified RNA (aRNA) containing sequences complementary to said target polynucleotide or via the promoter region of said third oligonucleotide to produce aRNA containing sequences present in said target polynucleotide.

18. The method of claim 17 wherein said formation of additional double stranded DNA templates from said aRNA further comprises degrading third oligonucleotides not used in c) i) or c) ii) with exonuclease activity before forming additional double stranded DNA templates.

19. The method of claim 17 wherein said target polynucleotide is mRNA.

20. The method of claim 17 wherein said more than one target polynucleotide are a cellular mRNA preparation.

21. The method of claim 17 wherein said first oligonucleotide comprises a primer containing an oligo or poly dT sequence.

22. The method of claim 21 wherein said oligo or poly dT sequence is at least about eight dT in length.

23. A method of amplifying RNA sequences complementary to one or more than one target polynucleotide that is single stranded or made single stranded, comprising a) forming double stranded cDNA templates containing sequences present in said target polynucleotide, wherein said sequences are operably linked to a promoter region, by i) annealing said one or more than one single stranded target polynucleotide with a first oligonucleotide comprising a primer operably linked to a promoter region to form a first complex, ii) synthesizing one or more than one first strand cDNA by reverse transcription of said first complex, iii) degrading first oligonucleotides not used in i) or ii) above with exonuclease activity, iv) annealing said one or more than one first strand cDNA, after denaturing the hybrid(s) of single stranded target polynucleotide and cDNA or degrading the single stranded target polynucleotide from said hybrid(s), with a plurality of second oligonucleotides comprising a random primer region comprising at least about six random nucleotides to form a population of second comprises, and v) forming one or more than one double stranded cDNA templates from said population of second complexes with DNA polymerase activity and b) transcribing said cDNA templates with an RNA polymerase capable of initiating transcription via said promoter region to produce amplified RNA (aRNA) containing sequences complementary to said one or more than one target polynucleotide.

24. The method of claim 23 wherein said random primer region comprises at least about nine random nucleotides.

25. The method of claim 17 wherein said DNA dependent DNA polymerase activity comprises exonuclease deficient Klenow and Taq polymerase activities.

26. The method of claim 17 wherein said third oligonucleotide comprises a random primer region.

27. The method of claim 26 wherein said random primer region comprises at least about six random nucleotides.

28. The method of claim 27 wherein said random primer region comprises at least about nine random nucleotides.

29. The method of claim 17 wherein said third oligonucleotide comprises a known primer sequence.

30. The method of claim 29 wherein said known primer sequence is complementary to the 3' region of said aRNA.

31. The method of claim 1, 10 or 17 wherein said first oligonucleotide comprises a T7 promoter region.

32. The method of claim 17 wherein said third oligonucleotide comprises a T3 or SP6 promoter region.

* * * * *